(12) United States Patent
Ellis et al.

(10) Patent No.: US 9,851,364 B2
(45) Date of Patent: Dec. 26, 2017

(54) ASSAY READER, DEVICE AND METHOD OF MEASURING HCG

(75) Inventors: Jayne Ellis, Little Addinton (GB); Jayne Marshall, Sandbach (GB); Stephen P. Sharrock, Bedford (GB)

(73) Assignee: ALERE SWITZERLAND GMBH, Zug (CH)

( * ) Notice: Subject to any disclaimer, the term of this patent is extended or adjusted under 35 U.S.C. 154(b) by 356 days.

(21) Appl. No.: 12/996,197

(22) PCT Filed: Jun. 3, 2009

(86) PCT No.: PCT/GB2009/050619
§ 371 (c)(1),
(2), (4) Date: Oct. 4, 2011

(87) PCT Pub. No.: WO2009/147437
PCT Pub. Date: Dec. 10, 2009

(65) Prior Publication Data
US 2012/0021531 A1    Jan. 26, 2012

(30) Foreign Application Priority Data
Jun. 4, 2008  (GB) .................................. 0810142.0

(51) Int. Cl.
*G01N 33/76*   (2006.01)
*G01N 33/68*   (2006.01)
(Continued)

(52) U.S. Cl.
CPC ....... *G01N 33/689* (2013.01); *G01N 21/8483* (2013.01); *G01N 33/54386* (2013.01);
(Continued)

(58) Field of Classification Search
CPC .... G01N 33/76; G01N 33/689; G01N 33/558; G01N 21/8483; G01N 2021/8488;
(Continued)

(56) References Cited

U.S. PATENT DOCUMENTS

| 5,026,653 A | 6/1991 | Lee et al. |
| 5,424,220 A | 6/1995 | Goerlach-Graw et al. |

(Continued)

FOREIGN PATENT DOCUMENTS

| DE | 202004008811 U1 | 9/2004 |
| DE | 102006003380 A1 | 8/2006 |

(Continued)

OTHER PUBLICATIONS

Sugantha et al., Predictive value of plasma human chorionic gonadotropin following assisted conception treatment, 2000, Human Reproduction, vol. 15, No. 2, pp. 469-473.*

(Continued)

*Primary Examiner* — Erik B Crawford
(74) *Attorney, Agent, or Firm* — David Halstead; Erik Huestis; Foley Hoag LLP

(57) ABSTRACT

Disclosed is a method for determining a quantitative estimate of the length of time since conception in a female mammalian subject, the method comprising: a) providing a liquid sample suspected of containing hCG; b) measuring, by means of an assay or assay device, an analyte measurement signal, whose value is dependent upon the level of hCG; c) comparing the measured signal value to an analyte threshold, wherein said analyte threshold corresponds to a time since conception; d) providing an quantitative estimate of the length of time since conception based upon the comparison in step (c).

26 Claims, 12 Drawing Sheets

Figure 1:
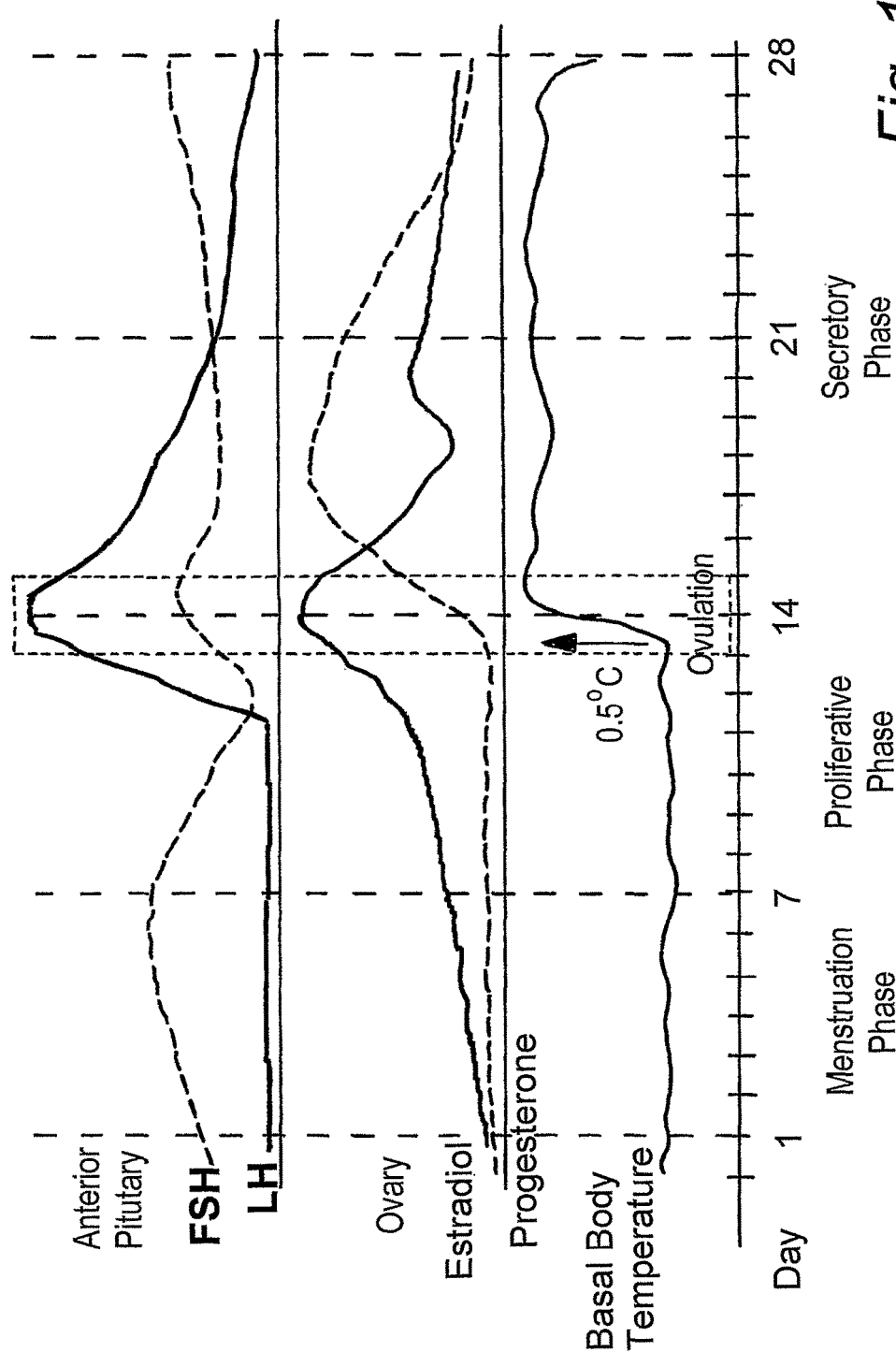

(51) Int. Cl.
    *G01N 33/558* (2006.01)
    *G01N 33/543* (2006.01)
    *G01N 21/84* (2006.01)

(52) U.S. Cl.
    CPC .......... *G01N 33/558* (2013.01); *G01N 33/76* (2013.01); *G01N 2021/8488* (2013.01); *G01N 2333/59* (2013.01)

(58) Field of Classification Search
    CPC .......... G01N 21/274; G01N 2021/7759; B01L 2300/0825
    USPC .................. 436/65, 510, 814, 815, 817, 818
    See application file for complete search history.

(56) References Cited

U.S. PATENT DOCUMENTS

| | | | |
|---|---|---|---|
| 5,707,818 | A | 1/1998 | Chudzik et al. |
| 5,731,212 | A | 3/1998 | Gavin et al. |
| 5,955,377 | A | 9/1999 | Maul et al. |
| 5,981,298 | A | 11/1999 | Chudzik et al. |
| 5,998,221 | A | 12/1999 | Malick et al. |
| 6,214,629 | B1 | 4/2001 | Freitag et al. |
| 6,297,020 | B1 | 10/2001 | Brock |
| 6,319,466 | B1 | 11/2001 | Markovsky et al. |
| 6,573,108 | B1 | 6/2003 | Hardman et al. |
| 6,656,745 | B1 | 12/2003 | Cole |
| 6,924,153 | B1* | 8/2005 | Boehringer et al. .......... 436/514 |
| 7,070,920 | B2 | 7/2006 | Spivey et al. |
| 7,144,742 | B2 | 12/2006 | Boehringer et al. |
| 7,303,923 | B2 | 12/2007 | Hardman et al. |
| 7,315,378 | B2 | 1/2008 | Phelan et al. |
| 7,713,748 | B2 | 5/2010 | Wei |
| 7,723,124 | B2 | 5/2010 | Aberl et al. |
| 7,989,217 | B2 | 8/2011 | Yee et al. |
| 2003/0207465 | A1 | 11/2003 | Davis et al. |
| 2004/0018576 | A1 | 1/2004 | DeMatteo et al. |
| 2004/0063219 | A1* | 4/2004 | Bateman et al. ............ 436/514 |
| 2004/0197820 | A1 | 10/2004 | Wei et al. |
| 2005/0036148 | A1* | 2/2005 | Phelan ........................ 356/446 |
| 2005/0037510 | A1* | 2/2005 | Sharrock et al. ............. 436/164 |
| 2005/0112779 | A1 | 5/2005 | Wei et al. |
| 2005/0112780 | A1 | 5/2005 | Song |
| 2005/0130120 | A1 | 6/2005 | Lambotte et al. |
| 2005/0170527 | A1 | 8/2005 | Boehringer et al. |
| 2005/0196812 | A1* | 9/2005 | Williams ....................... 435/7.1 |
| 2005/0196875 | A1 | 9/2005 | Blatt et al. |
| 2005/0208593 | A1 | 9/2005 | Vail et al. |
| 2006/0019404 | A1 | 1/2006 | Blatt et al. |
| 2006/0024842 | A1 | 2/2006 | Nylese |
| 2006/0199278 | A1 | 9/2006 | Leclipteux et al. |
| 2006/0246599 | A1 | 11/2006 | Rosenstein et al. |
| 2007/0020768 | A1 | 1/2007 | Rundstrom et al. |
| 2007/0042444 | A1 | 2/2007 | Niskanen et al. |
| 2007/0081920 | A1 | 4/2007 | Murphy et al. |
| 2007/0248983 | A1 | 10/2007 | Schwind et al. |
| 2009/0061534 | A1 | 3/2009 | Sharrock |
| 2010/0129935 | A1* | 5/2010 | Maddison .................... 436/510 |
| 2010/0206055 | A1 | 8/2010 | Abbott et al. |

FOREIGN PATENT DOCUMENTS

| | | |
|---|---|---|
| EP | 291194 A1 | 11/1988 |
| EP | 462376 A2 | 12/1991 |
| EP | 0465266 A1 | 1/1992 |
| EP | 1464613 A2 | 10/2004 |
| EP | 1484601 A2 | 12/2004 |
| EP | 1484641 A1 | 12/2004 |
| EP | 1571451 A1 | 9/2005 |
| GB | 2402474 A | 12/2004 |
| WO | WO-9706439 A1 | 2/1997 |
| WO | WO-2004021004 A1 | 3/2004 |
| WO | WO-2005/005991 A1 | 1/2005 |

OTHER PUBLICATIONS

Craig Medical Distribution Inc., Chart of hCG Hormone Ranges During Human Pregnancy, Oct. 11, 2007.*

Anonymous, "Clearblue Digital Pregnancy Test with Conception Indicator," SPD Swiss Precision Diagnostics GmbH, pp. 1-7 (Jul. 31, 2008). [online] XP002540666 (Retrieved from the Internet: URL:http://www.swissprecisionadiagnostics.com/downloads/Conception_Indicator_Tech_Brochure_final.pdf>.

Creinin Mitchell, D., et al.; "Accuracy of serum beta-human chorionic gonadotropin cutoff values at 42 and 49 days' gestation," American Journal of Obstetrics and Gynecology, 185(4):966-969 (Oct. 2001).

Kadar, Nicholas, et al.; "A prospective, randomized study of the chorionic gonadotropin-time relationship in early gestation: Clinical implications," Fertility and Sterility, 60(3):409-412 (1993).

Lagrew, D.C., et al.; "Accuracy of Serum Human Chorionic Gonadotropin Concentrations and Ultrasonic Fetal Measurements in Determining Gestational Age," American Journal of Obstetrics and Gynecology, 149(2):165-168 (1984).

Lenton, E. A., et al.; "Plasma Concentrations of Human Chorionic Gonadotropin from the Time of Implantation Until the 2nd Week of Pregnancy," Fertility and Sterility, 37(6):773-778 (1982).

ISR for PCT/GB2009/050619 dated Sep. 9, 2009.

McChesney, Ruth, et al. "Intact HCG, free HCG β subunit and HCG β core fragment: longitudinal patterns in urine during early pregnancy," Human Reproduction, 20(4):928-935 (Jan. 21, 2005).

Office Action in U.S. Appl. No. 13/312,447 dated Sep. 6, 2012.

Nepomnaschy, et al. "Urinary hCG patterns during the week following implantation," Human Reproduction, 23(2): 271-277 (2008).

Lopata, A., et al.; "Embryonic Development and Blastocyst Implantation Following In-Vitro Fertilization and Embryo Transfer," Fertility and Sterility, Elsevier Science Inc., New York, 38(6): 682-687 (Dec. 1, 1982).

Wilcox, A. J., et al.; "Time of Implantation of the Conceptus and Loss Pregnancy," New England Journal of Medicine, 340(23): 1796-1799 (Jun. 10, 1999).

EP Office Action for Application No. 09 757 809.0 dated Jun. 25, 2012.

ISR for PCT/GB2008/001227 dated Jun. 11, 2008.

European Search Report for EP 08252756.5 dated Sep. 22, 2011.

Examination Report for GB0815166.4 dated Sep. 30, 2011.

Office Action in U.S. Appl. No. 12/987,503 dated Jul. 30, 2013.

Author unknown, "Multiple Pregnancy," NICE (National Institute for Health and Care Excellence), http://www.nice.org.uk/guidance/cg129 (Sep. 2011).

Jurkovic, et al. "Diagnosis and management of ectopic pregnancy," BMJ, 342: d33397 (2011).

* cited by examiner

ASSAY READER, DEVICE AND METHOD OF MEASURING HCG

This application is a 371 national stage application of PCT/GB2009/050619, filed Jun. 3, 2009, which claims priority to GB 0810142.0, filed Jun. 4, 2008. The entire contents of each of these applications are hereby incorporated by reference.

FIELD OF THE INVENTION

The present invention relates to an assay device, reader, method and use of data for providing a time since conception.

BACKGROUND TO THE INVENTION

In the female reproductive system, the menstrual cycle is a recurring cycle of physiological changes and is necessary for reproduction that occurs in reproductive-age females. Menstrual cycles are counted from the first day of menstrual flow, because the onset of menstruation corresponds closely with the hormonal cycle and because menstrual bleeding is a readily apparent event for the individual concerned. The menstrual cycle may be divided into several phases, and the length of each phase varies from woman to woman and from cycle to cycle. The phases as well as their average values are typically as follows: the menstrual phase, days 1-4; the follicular phase (also known as proliferative phase), days 5-13; ovulation, day 14; the luteal phase, days 15-26 and the ischemic phase, days 27-28.

The follicular phase is the phase of the menstrual cycle during which follicles in the ovary mature. Through the influence of a rise in follicle stimulating hormone (FSH), about five to seven tertiary-stage ovarian follicles are recruited for entry into the next menstrual cycle. As they mature, the follicles secrete increasing amounts of estradiol. When the egg has matured, it secretes enough estradiol to trigger the acute release of luteinizing hormone (LH). In the average cycle this "LH surge" starts around cycle day 12 and may last about 48 hours. The release of LH matures the egg and weakens the wall of the follicle in the ovary. This process leads to ovulation. Estrogen levels continue to increase and are at their highest just before the LH surge begins. Most sources agree that ovulation normally occurs 24-48 hours after the beginning of the LH surge, typically about 36 hours after the LH surge.

The luteal phase is the latter phase of the menstrual cycle and begins with the formation of the corpus luteum and ends in either pregnancy or luteolysis. The main hormone controlling this stage is progesterone, which is significantly higher during the luteal phase than other phases of the cycle. The length of the follicular phase, and consequently the length of the menstrual cycle may vary widely; some women have a follicular phase of 10 days, others 16 days, while the average is 14 days. The luteal phase, however, almost always takes the same number of days for each woman. Normal sperm life inside a woman ranges from 1-5 days. The most fertile period (the time during which sexual intercourse is most likely to result in pregnancy) covers the time from some 5 days before ovulation until 1-2 days after ovulation. In an average 28 day cycle with a 14-day luteal phase, this corresponds to the second and the beginning of the third week of the cycle.

Following conception, β-hCG is secreted by the placenta and signals the corpus luteum to continue progesterone secretion, thereby maintaining the thick lining (endometrium) of the uterus. β-hCG continues to be secreted until placenta is able to secrete its own progesterone. The hCG hormone level in the human body doubles approximately every 2.2 days during the first trimester of pregnancy. If the egg is not fertilized, and therefore no β-hCG is produced, the corpus luteum stops secreting progesterone and decays. Without progesterone the uterine lining is expelled through the vagina (menses) and the menstrual cycle begins once more. Detectable levels of hCG in urine start at 5 mIU/ml during the first week of gestation and rise to 100,000 mIU/ml at 2 to 3 months. Values decline to 10% to 15% of peak concentrations during 2nd and 3rd trimesters. Thus, there is a very extended range of analyte concentration values.

Simple assay devices for determining the levels of hCG in urine are widely available for over the counter and professional use. Such devices are used to determine whether or not a woman is pregnant by measurement of the presence or absence of the hormone β-hCG. Nowadays, women will typically purchase such a device if they suspect they may be pregnant before consulting a healthcare professional.

However, once a woman establishes or suspects that she is pregnant, it is useful for her to know how many weeks pregnant she is. This can help her and the doctor or midwife plan for the future in estimating a date of birth of the baby as well, as well as plan a diary for other key dates such as the twelve week scan. Typically the doctor or midwife will determine the extent of pregnancy based upon knowledge obtained from the woman of the first day of her last menstrual period based on a standard 28 day cycle. Whilst the luteal phase is known to be fairly constant at around 15 days, the follicular phase may vary widely from for example between 9-28 days. Cycle lengths may vary widely from one woman to another. Thus basing the extent of pregnancy based upon the first day of her last period may vary widely in accuracy. Furthermore this assumes that the woman has given the correct date for her last menstrual period. Consequently estimates by the doctor concerning the extent of pregnancy based solely upon the levels of hCG can be quite inaccurate. Whilst a typical hCG assay test assay test can provide an indication of whether the subject is either pregnant or not pregnant, it cannot itself provide a further indication of the extent of pregnancy without requiring further specific information such as the date of a last missed period.

Simple immunoassay devices for measuring levels of analytes such as hCG in urine are widely available, for example sold under the name of Unipath Clearblue® Lateral flow immunoassay devices are also described in EP291194. Whilst such devices are able to indicate the presence or absence of hCG above or below a certain threshold, typically 10 or 25 mIU, and indicate that a subject is either pregnant or not pregnant, they are unable for determining levels of analyte over an extended analyte range such as levels of hCG ranging from 10 to 250,000 mIU.

In principle it is possible to measure levels of hCG over an extended range using a simple lateral flow type device. However, merely an indication of the amount of hCG in concentration based units would be of limited use to a healthcare professional in the absence of information as to the date of the last missed period and almost certainly of no use to the lay user.

Lateral flow devices such as described by EP291194 have been developed and commercialised for detection of a number of analytes in fluid samples. Such devices typically comprise a porous carrier comprising a dried mobilisable labelled binding reagent capable of binding to the analyte in question, and an immobilised binding reagent also capable of binding to the analyte provided at a detection zone downstream from the labelled binding reagent. Detection of the immobilised labelled binding at the detection zone provides an indication of the presence of analyte in the sample.

Alternatively, when the analyte of interest is a hapten, the immunoassay device may employ a competition reaction wherein a labelled analyte or analyte analogue competes with analyte present in the sample for an immobilised binding reagent at a detection zone. Alternatively the assay device may employ an inhibition reaction whereby an immobilised analyte or analyte analogue is provided at a detection zone, the assay device comprising a mobilisable labelled binding reagent for the analyte.

A sandwich immunoassay is often the assay of choice when detecting analytes. However, a sandwich assay is not always possible, for example in the case of small molecules such as haptens which may not be large enough to allow the simultaneous binding thereto of two different binding partners. A dose-response curve prepared using a typical lateral flow device employing a sandwich immunoassay shows increasing levels of signal with increasing analyte up to the point where at higher analyte levels the curve tends to plateau. At yet higher analyte levels, the signal begins to decrease due to preferential capture at the detection zone of analyte which has not yet bound to labelled reagent. This phenomenon is known as the hook effect. Thus, especially if a quantitative or semi-quantitative assay result is required, sandwich immunoassays exhibit a limited assay range due to the fact that the signal amount or intensity observed at higher analyte levels may be the same, or even less, than that observed at lower analyte levels.

A competition or inhibition assay typically provides a high signal at zero or low levels of analyte. At increasing levels of analyte the signal level may still be high depending upon the amount of labelled binding species present compared to the amount of analyte. At still increasing levels of analyte, the signal starts to decrease as unbound analyte either competes with labelled analyte or analyte analogue for the immobilised binding reagent or binds to labelled binding reagent, lowering binding of the labelled binding reagent at the detection zone.

So, use of sandwich assays to measure analyte over an extended range incurs problems with respect to the hook effect. High analyte concentrations start producing a reduction in assay signal. Competition or inhibition assays result in the depletion in assay signal at high analyte concentrations and thus offer a limited range over which analyte can be measured.

Thus the above assay methods are not suitable for measuring levels of analyte over an extended analyte range.

A number of assay devices have been proposed to measure analytes over an extended range.

US2004/0197820 discloses a flow through porous carrier assay device for reducing the hook effect comprising a detection zone wherein the device may include a downstream calibration zone.

US2006/0019404 discloses an assay device with an extended dynamic range comprising a lateral flow test-strip comprising a plurality of detection zones with a progressively decreased sensitivity to analyte concentration. The assay device may comprise two carriers each having a plurality of detection zones. The amount of label/signal present at the plurality of detection zones is detected to determine the analyte concentration.

EP462376 discloses an assay device comprising a capture site and a conjugate recovery site wherein the conjugate recovery site receives and binds said conjugate or conjugate complexes which migrate through said capture site and wherein immobilised conjugate at both the conjugate recovery site and capture site is detected to determine the amount of the analyte of interest.

Lateral flow type assay devices employing an optically detectable labelled binding reagent for the analyte or analyte analogue are the assay device of choice for simple, disposable assays. However a large number of other assay devices and methods may be employed to detect analytes. For example, the assay method may comprise a binding reagent for the analyte labelled with an enzyme, radioactive, electrochemically active or magnetic label. The analyte may be detected by means of an enzyme and an electrochemical mediator. Simple devices for the detection of glucose comprising the enzyme glucose oxidase and an electron mediator such as ferro/ferricyanide are widely commercially available. Acoustic biosensor type devices and methods, for example measuring the resonant frequency of a quartz crystal following a binding event, allow for the determination of an analyte without need to provide a labelled binding reagent.

SUMMARY OF THE INVENTION

According to a first aspect, the invention provides a method for determining a quantitative estimate of the length of time since conception in a female mammalian subject, the method comprising:
   a) applying a liquid sample suspected of containing hCG to an assay or assay device;
   b) measuring, by means of said assay or assay device, an analyte measurement signal, whose value is dependent upon the level of hCG;
   c) comparing the measured signal value to an analyte threshold, wherein said analyte threshold corresponds to a time since conception;
   d) providing an quantitative estimate of the length of time since conception based upon the comparison in step (c).

According to a second aspect, the invention provides an assay result reader for use with an assay or assay device for calculating a quantitative estimate of the length of time since conception in a female mammalian subject, the assay result reader comprising:
   a) a stored analyte threshold corresponding to a time since conception;
   b) a measurement means for measuring an analyte signal value corresponding to the level of hCG in a liquid sample obtained from said subject and to compare the analyte signal value to the stored analyte threshold, thereby providing an quantitative estimate of the length of time since conception based upon the comparison;
   c) a display means to display a time since conception.

In a third aspect, the invention provides an assay device for providing a quantitative estimate of the length of time elapsed since conception in a female mammalian subject, said assay device comprising:
   a) an assay result reader according to the second aspect of the invention;
   b) one or more assays for providing a signal value dependent upon the levels of hCG in a liquid sample.

An analyte threshold may be unique to a particular type of assay or assay device. An analyte threshold may be a signal value which corresponds to a time since conception.

An analyte threshold value for particular assay or assay device may be obtainable from the analysis of a first data set comprising levels of hCG measured as a function of time since conception, and a second date set relating the signal levels measured for that particular type assay or assay device as a function of hCG level.

The first data set is obtainable from the measurement of levels of hCG over time since conception in a cohort of pregnant female mammalian subjects.

The second data set may consist of one or (preferably) more data points.

The time since conception may be defined for example with respect to a particular event occurring during the menstrual cycle prior to conception. This event may be for example the time at which LH reached its maximum value or at which the LH surge occurred, at which the rise in basal body temperature (BBT) occurred, at which the second rise of FSH occurred or at which the rise of P3G (pregnanediol-3-glucuronide) occurred.

The time of conception may be a date of conception.

The date of conception may be defined for example as the date of the LH surge+x day/s, where x is a number.

In a fourth aspect, the invention provides for the use of a data set in the provision of an analyte threshold corresponding to a time since conception for use in the method according to the first aspect of the invention and/or in the assay reader according to the second aspect of the invention and/or in the assay device according to the third aspect of the invention, wherein the data set comprises hCG levels measured as a function of time since conception from samples of urine from a cohort of pregnant female mammalian subjects. In particular the data set may be used to derive one or more threshold values which are stored or entered in an electronic data processing means.

In particular the mammalian subject is human.

In particular the liquid sample is urine.

The first data set may be obtained from the measurement of levels of hCG over time from urine samples collected from a cohort of pregnant women who recorded the date of their LH surge in their previous menstrual cycle.

The second data set may be obtained from the testing of a particular type of assay or assay device with known concentrations of hCG and measuring the signal values for each level of hCG. A number of assay devices at each level of hCG may be tested in order to increase the number of data points.

From these first and second data sets, one or more threshold values may be obtained which are signal values corresponding to a time since conception. In order to increase the number of data points, a simulated data set may be generated if necessary. From the first and second data sets and/or from the simulated data set, a set of statistically optimised threshold values may be chosen to give the greatest clinical accuracy according to preselected time since conception classification criteria, for example a greater than 80% accuracy in a particular time classification range.

Due to the natural variation in hCG levels between pregnant women, different hCG values at each time point were observed from the first data set which had a particular distribution at each measured time. Consequently a chosen analyte threshold value represents an average signal value obtained for a particular data set. A different first data set obtained from a different cohort of women may result in a different analyte threshold. The threshold values were chosen on the basis that they provided an optimum clinical accuracy in providing a time since conception.

In order to determine the accuracy of the threshold values, the one or more chosen threshold values may then be used, for example by providing an assay device with the stored threshold values, to classify actual urine samples obtained from pregnant women. If necessary the threshold values may be refined in order to optimise the clinical accuracy of the classification.

The statistical analysis of the first data set may be carried out for example using an exponential model. The statistical analysis of the first data set may be carried out for example using a four parameter logistic curve. Other types of known statistical models may be employed to model and analyse the data.

An exemplary method which may be used to determine one or threshold values for an assay or assay device is described in Example 2 below. Example 2 describes the method by which threshold values were assigned to assay devices prepared according to Example 1, however the method could readily be applied to other types of assay devices.

The method, reader and assay device according to the first, second and third aspects may further comprise a further analyte measurement threshold indicative of a further time since conception. Similarly the data set according to the fourth aspect of the invention may be used to provide the second analyte measurement threshold. The further analyte threshold may be stored in the device or reader.

The assay device or reader may comprise two or more stored analyte thresholds, i.e. three, four or five corresponding to respective periods of time since conception. As an alternative to providing a plurality of individual measurement thresholds, the integral assay device or reader for use with an assay device may comprise a stored algorithm comprising a mathematical formula calculated to fit a data set relating to the signal values obtained for that equivalent assay device as a function of hCG level and therefore provide for any signal value a time since conception.

The method, reader and assay device according to the first, second and third aspects may further comprise a minimum pregnancy threshold (PDTmin) wherein an analyte measurement signal less than the minimum pregnancy threshold is indicative of being "not pregnant" and wherein an analyte measurement signal greater than the minimum pregnancy threshold is indicative of being "pregnant". The assay result may be provided at a time t<FDT, wherein FTD is the full development time of the assay, namely the maximum time over which the assay is measured.

A pregnant indication and a time since conception may be provided by the display means.

The time since conception may be provided in units of days, weeks or hours or it may provide a range of time, for example 2-3 weeks since conception, or 10+/−2 days since conception.

The first analyte threshold may correspond to a time since conception and a second analyte threshold may correspond to a later time since conception.

Thus for an analyte signal value of less than the first threshold, but greater than the minimum pregnancy threshold, a time since conception in a first time range may be indicated, an analyte signal value of greater than the second threshold may be indicated as a time since conception in a third time range, and an analyte signal value of greater than or equal to the first threshold but less than or equal to the second threshold may be indicated as being in a second time range occurring between the first and third time ranges.

According to an embodiment, the assay device comprises first and second analyte thresholds which correspond respectively to 14 days since conception and 21 days since conception. The result displayed by the display thus may be for example 1-2 weeks pregnant for an analyte signal value of less than the first analyte threshold but greater than the minimum pregnancy threshold, 3+ weeks pregnant for an analyte signal value of greater than the second analyte threshold and 2-3 weeks pregnant for an analyte signal value of greater than or equal to the first threshold but less than or equal to the second threshold.

The minimum pregnancy threshold value may be chosen depending upon the required sensitivity of the assay and thus for example may be set to correspond to a level of hCG corresponding to 5 mIU, 10 mIU, 15 mIU or 25 mIU or values in-between.

According to an embodiment the assay device or reader comprises a stored the minimum pregnancy threshold (PDTmin), a first analyte threshold (PDTmid) and a second analyte threshold (EPDTmax). The first analyte threshold may correspond to 14 days since conception and the second analyte threshold may correspond to 21 days since conception. For analyte measurement signals that are greater than EPDTmax, the assay result may be provided at a time t<FDT.

In a particular embodiment the recorded date which the time since conception is referenced is the timing of the LH surge. The timing of the LH surge is particularly useful as a time reference for the device and method according to the invention as it consistently occurs about 36 hours prior to ovulation and is a relatively precise predictor for timing ovulation.

The date of conception may be defined as the date of the LH surge+1 day.

As an alternative to providing a time since conception, an indication may be provided of the time since ovulation or the remaining gestation time (time to birth).

The display means may provide a "pregnant" or "not pregnant" indication by the respective display of the words "PREGNANT" OR "NOT PREGNANT" in any appropriate language, font or case. Alternatively a pregnant or not pregnant indication may be provided by an appropriate sign or symbol such as "+" or "−".

A result given by the integral assay device may differ from a result given by a healthcare professional had the pregnancy been dated based on a typical 28 day cycle based on the first day of the last period.

The assay device or reader may therefore be provided in combination with information relating the date of conception to the date of pregnancy based on a typical 28 day cycle based on the first day of the last period. This information may be provided for example on the packaging in which the integral assay device or reader is provided or on an information leaflet provided along with the device.

Typically for an indication of a time of since conception for a pregnant indication by the device, that time plus 2 weeks will be given as how the healthcare professional will date the pregnancy.

For example the information may be given as follows:

| Time since conception given by the assay device or reader | How your doctor will date your pregnancy based on a 28 day cycle |
|---|---|
| Your result is Pregnant and you conceived approximately 1-2 weeks ago. | 3-4 weeks |
| Your result is Pregnant and you conceived approximately 2-3 weeks ago. | 4-5 weeks |

-continued

| Time since conception given by the assay device or reader | How your doctor will date your pregnancy based on a 28 day cycle |
|---|---|
| Your result is Pregnant and you conceived more than 3 weeks ago. | 5+ weeks |

The date at which the doctor would date a pregnancy based on a 28 day cycle may be provided by the assay device or reader instead of or in addition to providing a time since conception.

In the method according to the first aspect, the assay by which hCG levels may be determined for example by an immunoassay laboratory analyser or an ELISA 96 well plate.

The assay device according to the first and third aspects of the invention may conveniently comprise a flow through or lateral flow type immunoassay capable of measuring hCG over an extended analyte range. Other types of assay are contemplated such as an acoustic biosensor immunoassay, or a microfluidic type immunoassay.

In particular the assay is a lateral flow assay. The assay device may be single use, i.e. disposable.

Due to the increase in hCG over time since conception, wherein levels of hCG, start at 5 mIU/ml during the first week of gestation and rise to 100,000 mIU/ml at 2 to 3 months, the assay device needs to be able to measure hCG over an extended analyte range.

The assay device may comprise a single assay flow path capable of measuring hCG or two or more assay flow-paths each capable of measuring hCG over a different concentration range.

The assay flow path may comprise a porous carrier comprising a detection zone for detecting a labelled binding reagent for hCG analyte.

The assay flow-path may comprise a mobilisable (i.e. mobilisable upon contact with a liquid sample, such as urine) labelled binding reagent which is capable of being captured or immobilised at the detection zone. The labelled binding reagent may be provided upstream from the detection zone. The labelled binding reagent may be provided in the dry state. The detection zone may comprise an immobilised binding reagent which is capable of immobilising a labelled binding reagent.

The term binding reagent refers to a member of a binding pair. The binding reagent may comprise an antibody or an antibody fragment, capable of binding to hCG. The analyte hCG comprises an alpha sub-unit identical to that of luteinising hormone (LH), follicle stimulating hormone (FSH) and thyroid stimulating hormone (TSH) and a beta sub-unit unique to hCG. Antibodies to the alpha and beta sub-units may be used to bind to hCG in a sandwich immunoassay format.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

"Label" when used in the context of a labelled binding reagent, refers to any substance which is capable of producing a signal that is detectable by visual or instrumental means. Various labels suitable for use in the present invention include labels which produce signals through either chemical or physical means, such as being optically detectable. Such labels include enzymes and substrates, chromogens, catalysts, fluorescent compounds, chemiluminescent compounds, electroactive species, dye molecules, radioactive labels and particle labels. The analyte itself may be inherently capable of producing a detectable signal. The label may be covalently attached to the binding reagent.

The label may comprise a particle such as gold, silver, colloidal non-metallic particles such as selenium or tellurium, dyed or coloured particles such as a polymer particle incorporating a dye, or a dye sol. The dye may be of any suitable colour, for example blue. The dye may be fluorescent. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. According to an exemplary embodiment the label is a blue polymeric particle.

The term assay flow-path refers to a substrate that is able to convey a liquid from a first position to a second position and may be for example a capillary channel, a microfluidic pathway, or a porous carrier such as a lateral flow porous carrier. The porous carrier may comprise one or a plurality of porous carrier materials which may overlap in a linear or stacked arrangement or which are fluidically connected. The porous carrier materials may be the same or different. The first and second flow paths may be provided on separate substrates or they may be provided on a common substrate such that liquid being conveyed along a flow-path of the first assay is not able to cross over to the flow-path of the second assay. For example, the first and second assays may be provided on the same porous carrier such that the first and second flow-paths are isolated from each other. This may be achieved for example by laser cutting parts of the porous carrier to make it non-porous, thus separating the first and second flow-paths. As yet a further alternative, the first and second detection zones may be provided on the same flow-path in substantially a side by side arrangement, such that neither is provided downstream from the other.

In particular the flow-path may comprise a lateral flow porous carrier. The labelled binding reagent and detection zone of the assay may be provided respectively on different carrier materials. Suitable materials that may be employed as a porous carrier for providing the detection zone include nitrocellulose, acetate fibre, cellulose or cellulose derivatives, polyester, polyolefin or glass fibre. The porous carrier may preferably comprise nitrocellulose. This has the advantage that a binding reagent can be immobilised firmly without prior chemical treatment. If the porous solid phase material comprises paper, for example, the immobilisation of the antibody in the second zone needs to be performed by chemical coupling using, for example, CNBr, carbonyldiimidazole, or tresyl chloride.

The assay may be provided in the form of a test-strip.

The assay device may comprise a control zone. The control zone may be provided downstream from the detection zone. The assay device may further comprise a labelled binding reagent for the control zone provided upstream from the detection zone. Measurement of the signal at the control zone indicates whether the assay test has been carried out satisfactorily, namely the reagents were present in the test device and that they become mobilised during running the test and have been transported along the flow path. The control zone can also indicate that the reagents within the device are capable of immunochemical interactions, confirming the chemical integrity of the device. This is important when considering the storage and shipment of the device under desiccated conditions within a certain temperature range. The control zone is typically positioned downstream from the detection zone. The control zone may comprise immobilised binding reagent for a labelled binding reagent. The labelled binding reagent may be the same binding reagent that binds to the detection zone or it may be a different binding reagent. The immobilised binding reagent at the control zone may for example be an anti-species antibody to a labelled binding reagent raised in a species, e.g. an "anti-mouse" antibody if the labelled antibody is one that has been derived using a murine hybridoma.

The assay device or reader may comprise a stored control signal threshold (CLT) wherein a signal measured at the control zone is compared to the control threshold to indicate whether the assay has been carried our satisfactorily.

The assay device or reader may further comprise a stored minimum analyte threshold wherein if the measurement signal is less than the minimum threshold by a minimum analyte threshold time, it is determined that the measurement signal will never reach the measurement threshold by the full assay development time. This would represent the case of a liquid sample having a very low or non-existent analyte concentration. In this case an early negative indication, namely an indication of the absence of analyte or the absence of analyte above a certain minimum level, may be provided at a time t<FDT.

The assay device and reader may comprise one or more of the following: a central processing unit (CPU) or microcontroller; one or more LEDs; one or more photodetectors; a power source; and associated electrical circuitry. The power source may be a battery or any other suitable power source (e.g. a photovoltaic cell). Conveniently the CPU or microcontroller will be programmed so as determine, from the output of the photodetectors, the rate or amount of signal accumulation and to compare this to the control and measurement thresholds.

The assay device and reader may comprise a timing means by which to measure the time of the assay and by which to determine the time of commencement of measurement of the assay. The timing means may for example comprise a sample presence indication means to detect the time at which liquid sample is added to the device such as a pair of electrodes which are able to detect the presence of liquid sample. Alternatively the timing means may be comprised as part of the optical detection means, wherein timing of the assay measurement is commenced at the time liquid sample is determined by the photodetector as having reached a particular zone of the assay flow-path.

The assay device and display may further comprise a display means to display the result of the assay. The display means may further display further information such as an error massage, personal details, time, date, and a timer to inform the user how long the assay has been measured for. The information displayed by the assay may be indicated in words, numbers or symbols, in any font, alphabet or language, for example, "positive", "negative", "+", "−", "pregnant", "not pregnant", "see your doctor", "repeat the test".

The assay device and reader may comprise a signal detection means to determine the extent and/or amount of labelled species present at the detection and control zones. The signal detection means may comprise an optical detection means such as a photodetector to determine the extent and/or amount of labelled species present. The assay device may comprise one or more light sources such as an LED positioned so as to optically illuminate the zones. Light from the light source illuminates the respective zones and is either transmitted or reflected onto a photodetector which records the amount or intensity of the transmitted or reflected light. The presence of labelled binding reagent at the zones will influence the amount of light that is either transmitted or reflected, thus measurement of light at the photodetector is indicative of the presence or amount of the labelled binding reagent.

A suitable light source is an LED. The colour of the LED will be determined by the colour of the labelled binding reagent. For a blue label, a suitable colour for the LED is red. The LED may be illuminated at a particular frequency or frequencies in order to illuminate a particular zone of the assay device. Light is reflected or transmitted from the zone onto a photodetector which records an electrical signal. The number of electrical signals recorded will depend upon the operating frequency of the LED and thus one or more signals may be recorded over time. The signals will typically be expressed as a % absorbance (% A).

Each measurement zone is typically illuminated by a single LED. A photodetector may detected light from one than one measurement zone and therefore reflected light from one than one LED. This may be achieved by carrying out the illumination process sequentially such that device is able to know which from which zone light is being reflected from onto the photodetector. The sequential illumination process may be repeated with a fixed or varied frequency during the duration of the assay such that the levels of signal over time at each zone may be monitored.

The assay device may comprise a means to detect the time addition of fluid sample. For example, the change in levels of light detected from one or more zones may be monitored to determine whether and when a fluid sample has been applied to the device. The timing of the assay test may be started automatically for example when liquid sample has reached a particular zone.

The assay device and reader may comprise a flow control means wherein the change in levels of light detected from one or more zones may be used to determine whether and when a fluid sample has been applied to the device and to determine the flow-rate of liquid sample along the device by measurement of flow between one or more measured zones. Determination of the flow-rate may be used as a further quality control check, for example the assay may be rejected if the flow-rate is either greater than or less than set levels. The computation circuit may be responsive to the signals to calculate a flow rate for a fluid flowing along the carrier, compare the calculated flow rate to upper and lower limits, and reject the assay result if the calculated flow rate is outside the upper and lower limits.

The typical optical detection and illumination system will comprise at least one light source and at least one photodetector (such as a photodiode). Preferred light sources are light emitting diodes or LEDs. Reflected light and/or transmitted light may be measured by the photodetector. For the purposes of this disclosure, reflected light is taken to mean that light from the light source is reflected from the porous carrier or other liquid transport carrier onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

The assay device will typically comprise one or more apertures or windows through which light may shine from the one of more sources of illumination onto a particular zone of the assay or assay strip. The windows serve to define the area of light falling onto a particular zone and to define which part of the assay or assay strip is illuminated. Each zone to be illuminated may have a corresponding window. Thus a device having four measurement zones will have four windows. Light reflected from the windows is collected by the one or more photodetectors. For an assay device comprising a flow path having a plurality of zones the time taken for the liquid sample to travel between the zones may be measured.

In addition to measuring the detection zones of the respective assays as well as the control zones where present, the optical means may also measure a reference zone, namely a portion of the flow-path which is free from binding reagent in the dry state. The purpose of the reference zone is to provide a signal value against which the signal value obtained at the detection zone may be compared. Measurement of the reference zone enables measurement of the background levels of reflected or transmitted light from the flow-path. The background level may be due for example to the optical reflectance of the porous carrier, the presence of liquid sample, or of components of the assay such as a labelled binding reagent. The levels of light measured at the detection zone may therefore be corrected with respect to the levels of background light to provide a compensated signal indicative of the amount of labelled binding reagent present at the detection zone. Measurement at the reference zone may also compensate for any variation between fluid samples applied to assay devices, for example urine samples may vary widely in colour.

The assay will typically take place over a time during which labelled binding reagent accumulates at the test and control zones. A typical time for an assay test is 3 minutes.

Measurements of the light reflected from each window may be taken periodically (for example approximately twice a second) and a low pass digital filter may be used to reject noise and smooth the data. Filtered values may be used for detecting flow and determining the assay result.

For each window, a ratio may be calculated of the measured value when the particular measurement zone in the flow-path is dry ("calibration value"), namely before any liquid sample has reached said zone, divided by the measured value when the measurement zone is wet and a line may have developed. This ratio equals the proportion of light reflected after the change in the reflective properties of the flow-path as a consequence of the liquid sample passing along the flow-path. For example when the flow-path comprises a porous carrier such as nitrocellulose the change in reflective properties can be quite marked.

For each window, the window ratio at the reference, control, and test windows is equal to the measured value when the porous carrier is dry, t=0 (prior to addition of sample), divided by the measured value at time t after addition of sample:

For each time point t the window ratios for each window may be evaluated as follows:

$$Ref\ ratio_t = \frac{\text{filtered reference window } value_{time=0}}{\text{filtered reference window } value_{time=t}}$$

$$Test\ ratio_t = \frac{\text{filtered test window } value_{time=0}}{\text{filtered test window } value_{time=t}}$$

$$Ctrl\ ratio_t = \frac{\text{filtered Ctrl window } value_{time=0}}{\text{filtered Ctrl window } value_{time=t}}$$

Calculation of Filtered % A Values

For each time point t. % A values may calculated using these ratios for a test line and a control line using the reference ratio as a baseline for the background that would have occurred in all windows had a line not developed.

$$Test_t(\%\ A) = \frac{Ref\ ratio_t - test\ ratio_t}{Ref\ ratio_t} \times 100\%$$

$$Ctrl_t(\%\ A) = \frac{Ref\ ratio_t - Ctrl\ ratio_t}{Ref\ ratio_t} \times 100\%$$

The assay device may a high sensitivity (HS) assay for the detection of analyte in a lower concentration range comprising a detection zone and low sensitiovity assay (LS) for the detection of analyte in a lower concentration range the assay device comprising a test zone, a reference zone and a control zone. Signals measured at both the HS and LS zones may be defined as follows:

$$HS\ ratio_t = \frac{\text{filtered HS test window } value_{time=0}}{\text{filtered HS test window } value_{time=t}}$$

$$LS\ ratio_t = \frac{\text{filtered LS test window } value_{time=0}}{\text{filtered LS test window } value_{time=t}}$$

The filtered % A values may be defined for the HS and LS zones as follows:

$$HS_t(\%\ A) = \frac{Ref\ ratio_t - HS\ test\ ratio_t}{Ref\ ratio_t} \times 100\%$$

$$LS_t(\%\ A) = \frac{Ref\ ratio_t - LS\ test\ ratio_t}{Ref\ ratio_t} \times 100\%$$

Typically the % A values will be those obtained at the full assay development time although values may be determined at times t<FDT.

The normalised percentage relative attenuation (% A) is given by the difference of the reference window ratio and the window ratio being considered (control or test windows) divided by the reference window ratio and multiplied by 100%.

Control and measurement signal values may be presented as % A, namely the signal value with respect to the signal measured at a reference zone.

Alternatively, signal values may be presented as % R, namely an absolute value.

Flow Detection and Validation

Flow Detection

The window ratio for each window may be used to detect the flow of fluid past the window. Flow is classed as having reached a window when the ratio has dropped by the Flow Detection Threshold Percentage (FDT %). This corresponds to an increase in the filtered value over its calibration value by the same proportion.

$$\text{For time } t, \text{Window ratio} \geq \frac{1}{1 + FDT\ \%}$$

or $$\frac{\text{filtered } value_{time=t}}{\text{filtered } value_{time=0}} \geq 1 + FDT\ \%$$

The time for each window when the criterion is first satisfied is recorded for flow validation.

Flow Validation

Various parameters corresponding to flow may be stored within the assay device or reader and used to classify flow of liquid sample along porous carrier of an assay device. The device or reader may display any errors in flow.

The assay device or reader may comprise one or more stored values corresponding to a minimum flow detection time, $FDT_{min}$, a maximum flow detection time, $FDT_{max}$, a minimum window transit time $MTT_{min}$ and a flow detection threshold, FDTh.

The assay device or reader may comprise one or more additional stored values such as a full assay development time of the assay (FDT), a minimum assay development time (MDT), and an early pregnant maximum decision threshold (EPDTmax).

The assay result may be provided only after a minimum assay development time (MDT) has elapsed. MDT may be zero.

A stored threshold or value may be stored permanently in the device or reader or transiently. It may be imported into the device or reader from an external device.

The assay device may comprise a porous sample receiver in fluid connection with and upstream from the flow-path. The assay device may comprise more than one assay flow-path each comprising a detection zone, in which case a single porous sample receiver may be provided which is common to the multiple assay flow paths. Thus a fluid sample applied to the porous sample receiver of the device is able to travel along the flow-paths of the respective assays to the respective detection zones. The porous sample receiver may be provided within a housing or may at least partially extend out of said housing and may serve for example to collect a urine stream. The porous sample receiver may act as a fluid reservoir. The porous sample receiving member can be made from any bibulous, porous or fibrous material capable of absorbing liquid rapidly. The porosity of the material can be unidirectional (i.e. with pores or fibres running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fibre.

If desired, an absorbent "sink" can be provided at the distal end of the carrier material. The absorbent sink may comprise of, for example, Whatman 3MM chromatography paper, and should provide sufficient absorptive capacity to allow any unbound labelled binding reagent to wash out of the detection zone. As an alternative to such a sink it can be sufficient to have a length of porous solid phase material which extends beyond the detection zone.

Following the application of a binding reagent to a detection zone, the remainder of the porous solid phase material may be treated to block any remaining binding sites. Blocking can be achieved by treatment for example with protein (e.g. bovine serum albumin or milk protein), or with polyvinylalcohol or ethanolamine, or combinations thereof. To assist the free mobility of the labelled binding reagent when the porous carrier is moistened with the sample, the porous carrier may further comprise a sugar such as sucrose or lactose and/or other substances, such as polyvinyl alcohol (PVA) or polyvinyl pyrrolidone (PVP). Such material may be deposited for example as an aqueous solution in the region to which the labelled binding reagent is to be applied. Such materials could be applied to the porous carrier as a first application followed by the application of the label, alternatively such materials could be mixed with the label and applied to the porous carrier or combinations of both. Such material may be deposited upstream from or at the labelled binding reagent.

Alternatively, the porous carrier may not be blocked at the point of manufacture; instead the means for blocking the porous carrier are included in a material upstream from the porous carrier. On wetting the test strip, the means for blocking the porous carrier are mobilised and the blocking means flow into and through the porous carrier, blocking as the flow progresses. The blocking means include proteins such as BSA and casein as well as polymers such as PVP, PVA as well as sugars and detergents such as Triton-X100. The blocking means could be present in the macroporous carrier material.

The nitrocellulose porous carrier may have a pore size of at least about 1 micron, for example greater than about 5 microns, and for example about 8-12 microns.

The nitrocellulose porous carrier may be backed e.g. with a plastics sheet, to increase its handling strength. This can be manufactured easily by forming a thin layer of nitrocellulose on a sheet of backing material such as Mylar™.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastics materials such as polyethylene and polypropylene, or other materials such as paper or glass-fibre. In the case that the labelled binding reagent is labelled with a detectable particle, the macroporous body may have a pore size at least ten times greater than the maximum particle size of the particle label. Larger pore sizes give better release of the labelled reagent. As an alternative to a macroporous carrier, the labelled binding reagent may be provided on a non-porous substrate provided upstream from the detection zone, said non-porous substrate forming part of the flow-path.

The porous carrier may comprise a glass-fibre macroporous carrier provided upstream from and overlapping at its distal end a nitrocellulose porous carrier.

The assay device typically comprises a housing containing the assay/s. The housing may be fluid impermeable and constructed from a suitable plastics material, such as ABS. The assay may further comprise a sample receiving member for receiving the fluid sample. The sample receiving member may extend from the housing.

The housing may be constructed of a fluid impermeable material. The housing will also desirably exclude ambient light. The housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively the aperture may serve to allow a porous sample receiver to extend from the housing to a position external from the housing.

An assay device comprising two or more assays may have a shared reference zone, wherein the value of the signal obtained at the reference zone for one assay is used to compensate the value of the signal obtained at the detection zone for the other assay. As such the reference zone is "shared" between both assays.

An assay device comprising two or more assays may have a shared control zone wherein measurement of the signal at the control zone of one assay provides a value or indication that the test has been carried out correctly (or incorrectly) for that assay as well as for the other assay. If for example, the control zone indicates that the test has been carried out correctly for one assay, a decision is made by the assay device that the test has been carried out correctly at the other assay. Hence the control zone may be thought of as being "shared" between the assays of the assay device.

An assay device may comprise a shared control zone and a shared reference zone.

The assay device may further comprise one or more measurement overflow parameters, wherein if any of the measurements is greater or much less than a value that would have been expected, the result will be rejected. This enables the assay device to reject for example, hardware failures such as a break or shorting in the circuit board, a flat battery, a blocked optical window, a failed LED and so on.

The assay device may for example comprise two or more flow-paths each comprising a detection zone for the detection of hCG.

There are many different ways to provide an assay device capable of measuring hCG analyte over an extended range. The assay device may be provided in the form of for example a "ladder" or "spill-over" assay, wherein any labelled binding reagent that is not immobilised at the a first detection zone proceeds to a second downstream detection zone. The respective detection zones may comprise immobilised binding reagents having differing binding affinities for a labelled binding reagent-analyte complex.

The assay device may comprise a high sensitivity first assay capable of measuring hCG in a lower analyte range and a low sensitivity assay capable of measuring hCG in a higher analyte range.

In order to measure hCG in a higher analyte range, the assay device may for example comprise a labelled binding reagent for the analyte and a second binding reagent for the analyte, provided upstream from the detection zone. The second binding reagent serves to remove excess analyte and lower the sensitivity of the assay. This has the effect of increasing the dynamic range of the assay enabling measurement at higher analyte levels. The second binding reagent may be may be immobilised, mobilisable or both. The second binding reagent may be provided at either the same region of the porous carrier as the mobilisable labelled binding reagent, upstream from it or downstream from it. The second binding reagent may bind to the same binding region of the analyte as the mobilisable labelled binding reagent or to a different region of the analyte than the labelled binding reagent. The second reagent may have a different affinity for the analyte than the mobilisable labelled binding reagent of the second assay. In an exemplary embodiment, the second binding reagent has a higher affinity for the analyte than the mobilisable binding reagent of the second assay. The amount of second binding reagent may be varied to change the sensitivity of the assay to analyte concentration. Increasing the amount of second binding reagent present lowers the sensitivity of the assay due to the fact that the second binding reagent is able to bind more analyte, effectively lowering the proportion of labelled binding reagent that is able to bind to the detection zone.

In order to increase the dynamic range of the assay, the assay device may for example comprise multiple detection zones, wherein each detection zone is capable of binding analyte at different analyte concentration levels. For example the respective zones may comprise binding reagent for the analyte having a differing affinities for the analyte.

Other ways to increase the dynamic range of the assay are to provide an assay device comprising a sandwich binding assay and a competition or inhibition assay. For example, the sandwich assay may be the high sensitivity assay, namely it is capable of measuring analyte at a lower concentration range and the inhibition or competition assay may be a low sensitivity assay, namely it is capable of measuring analyte at a higher concentration range. A further way is to alter the affinity or amount of the labelled binding reagent or the immobilised reagent at the detection zone. A high affinity binding reagent will have a higher analyte sensitivity than a lower affinity binding reagent. Similarly a low concentration of binding reagent will have a lower analyte sensitivity than a high concentration of binding reagent. The assay sensitivity can be changed by altering the ratio of binding reagent to the label of the labelled binding reagent. If a particle is used as the label, then the quantity of the binding reagent applied to the label can be altered to alter assay sensitivity. A further way to manipulate the sensitivity of an assay is to vary the quantity of the label used in the assay. For example the sensitivity of an assay may be lowered by reducing the ratio of binding reagent to labelled species for the labelled binding reagent.

A further means of manipulating the sensitivity of an assay is to alter the optical density of a label. The assay sensitivity can be lowered by use of a label with a low optical density. This may be achieved for example by provision of a polymer particle label having a low concentration of dye or by use of a coloured label which is less sensitive to an optical detector.

Yet a further way to measure high analyte levels is to employ a non-particulate labelled binding reagent. High levels of analyte when measured by way of a sandwich binding assay may require high levels of binding reagent. In the case wherein the label is a particle label, provision of high levels of analyte within or on the porous carrier can give rise to steric hindrance resulting in poor assay sensitivity. Conversely, at lower analyte levels, the use of a non-particle labelled binding reagent can give rise to a low signal due to the low optical density. However, at high analyte levels, non-particle labels may be present at sufficiently high levels to be readily detected. An example of a optically detectable non-particulate label may be a dye. The dye may be fluorescent.

Assay sensitivity may be influenced by the flow rate of the porous carrier. A way to lower the sensitivity of the assay is to employ a porous carrier (such as nitrocellulose) having a higher flow rate.

The sensitivity of an assay may be further manipulated by modifying the rate at which the labelled binding reagent is released from its origin. A further way to lower analyte sensitivity is to provide for a rapid release of the labelled binding reagent from the porous carrier during contact with the liquid sample. The release of the labelled binding reagent can be modified by the provision of sugars, proteins or other polymeric substances such as methylcellulose within the device.

During the course of their investigations into measurement of hCG over an extended analyte range, the inventors constructed a number of different devices including a number according to the prior art. They found that whilst a number of such devices were found to be satisfactory at measuring analytes, they suffered from limitations in their ability to measure levels of analytes over an extended analyte range sufficiently accurately enough to satisfy the regulatory requirements in order to make the device suitable for commercial purposes. The present inventors have shown that for assay devices wherein multiple detection zones for the detection of an analyte are provided on the same porous carrier, the binding at an upstream detection zone may change the binding characteristics at a downstream detection zone and that any variation in binding at an upstream detection zone may cause a compounded variation of binding at a downstream detection zone. This is especially so at higher analyte concentration levels and can give rise to poor assay precision. Furthermore, it has been found that cross-binding may occur between the respective binding reagents present in the detection zones during running of the test and cross-binding has also been observed during manufacture of the devices and whilst they are stored in the dry state. This was shown to have an impact on the levels of assay precision and sensitivity. These problems do not appear to have been recognised previously in the prior art.

According to an embodiment, the assay device comprises a first assay and a second assay, wherein the first assay for the determination of hCG analyte comprises a first flow-path having a sole detection zone capable of immobilising a labelled anti-hCG binding reagent and the second assay for said analyte comprises a second flow-path having a sole detection zone capable of immobilising a labelled anti-hCG binding reagent, wherein the presence of the labelled binding reagent at the detection zones provides an indication of the presence and/or extent of hCG analyte in said liquid sample.

The first assay may provide an indication of the level of hCG analyte in a first concentration range and the second assay may provide an indication of the level of hCG analyte in a second concentration range.

The first and second concentration ranges differ from each other. The first and second concentration ranges may overlap so as to provide a continuous concentration range.

The first and second assays may either independently or together provide an indication of the level of hCG analyte within a certain concentration range.

As an alternative to providing the first and second assays within a single assay device, the assays may be provided as separate assay devices, the results from the respective devices when taken together being capable of providing an indication or measurement of the level of analyte.

The liquid sample may be chosen from blood, serum, plasma and urine. In particular the sample is urine.

The integral assay device of the invention may be used to measure the extent or presence of hCG over an extended concentration range. The range may vary from between about 10 mIU to about 250,000 mIU.

In a further embodiment, the integral assay device comprises two porous carriers each having a single detection zone, the device comprising a shared reference zone and a shared control zone, wherein the assay device further comprising a single photodetector arranged to receive light from the four zones and four light emitting diodes.

In particular the assay device comprises two assays, a high sensitive assay, namely the assay is sensitive to levels of analyte at a low analyte concentrations, and a low sensitive assay, namely the assay is sensitive to analyte at higher analyte concentrations.

In a particular embodiment the assay device comprises a first assay flow-path comprising a mobilisable labelled binding reagent for hCG provided upstream from a detection zone and a second assay flow-path comprising a mobilisable labelled binding reagent for hCG and a second binding reagent for hCG provided upstream from a detection zone. The second labelled binding reagent may be provided in the same region or in the vicinity of the labelled binding reagent. The second binding reagent may be immobilised or mobilisable. In an embodiment, the second binding reagent is mobilisable. The second binding reagent may bind to the same binding region of the analyte as the mobilisable labelled binding reagent or to a different region of the analyte than the labelled binding reagent. In particular the second binding reagent is capable of binding to the beta-subunit of hCG, and the mobilisable labelled binding reagent is capable of binding to the alpha-subunit of hCG. The amount of second binding reagent may be varied to alter the sensitivity of the assay.

According to an embodiment, the assay device comprises two assay test-strips each having a detection zone. A shared control zone is provided on one assay strip and a shared reference zone is provided on the other assay strip. The value of the signal obtained at the reference zone for one assay is used to compensate the value of the signal obtained at the detection zone for the other assay. As such the reference zone is "shared" between both assays.

The provision of a shared reference and/or control zone reduces the number of optical components required for the assay device as each reference and/or control zone would require an illumination source such as an LED.

By employing a shared reference and/or control zone, the assay device may reduce the number of zones that need to be detected and consequently the number of optical components that need to be employed. The use of shared zones is most effective when the assay architectures of the first and second assays are similar or, if the reference and/or control zone is provided on one or more subsidiary flow-paths, when the assay architecture of the one or more subsidiary flow-paths is similar to the first and second assays. It is also advantageous to use the same liquid sample for each assay. This may be conveniently achieved by providing a common sample application region that is in fluid communication with both assays. Thus a single liquid sample applied to the device via the common sample application region may flow through both the first and second assays. In cases where the first and second assays are non-identical, it may be acceptable to provide a shared reference zone as long as background levels of light that would be detected at each assay are sufficiently similar to each other.

The shared reference zone may be comprised as part of either the first or second assay. Alternatively the reference zone may be provided on a subsidiary flow-path to the first and second assay. The reference zone may be chosen from a portion of the flow-path not corresponding to a detection zone, or, where a dried labelled reagent is present upstream from the detection zone, a portion not corresponding to where the dried labelled reagent is present.

In an embodiment the assay device comprises a first high sensitivity analyte assay comprising a shared reference zone and a second low sensitivity analyte assay comprising a shared control zone. The low sensitivity assay may comprise a higher amount of labelled binding reagent than the higher sensitivity assay. The high sensitivity assay may comprise a an flow-path comprising a labelled binding reagent for hCG provided upstream from a detection zone and a the low sensitivity assay may comprise a labelled binding reagent for hCG and a second binding reagent for hCG provided upstream from a detection zone.

The reference zone may be provided downstream or upstream from the detection zone. Measurement of the reference zone enables measurement of the background levels of reflected or transmitted light from the flow-path. The background level may be due for example to the optical reflectance of the porous carrier, the presence of liquid sample, or of components of the assay such as a labelled binding reagent. The levels of light measured at the detection zone may therefore be corrected with respect to the levels of background light to provide a compensated signal indicative of the amount of labelled binding reagent present at the detection zone. Measurement at the reference zone also compensates for any variation between fluid samples applied to assay devices, for example urine samples may vary widely in colour. The value of the signal obtained at the reference zone for one assay is used to compensate the value of the signal obtained at the detection zone for the other assay. As such the reference zone is "shared" between both assays. The provision of a shared reference zone reduces the number of optical components required for the assay device as each reference zone would require an illumination source such as an LED.

The assay device may comprise more than two assays, such as three, four or five assays wherein the device has one or more shared reference zones.

Aspects of the invention are further illustrated by reference to the following figures:

FIG. 1 shows the variation in hormone levels and basal body temperature that occurs during a typical 28 day menstrual cycle.

FIGS. 2 (a) and (b) show an exemplary assay device of the invention.

Figure 3:
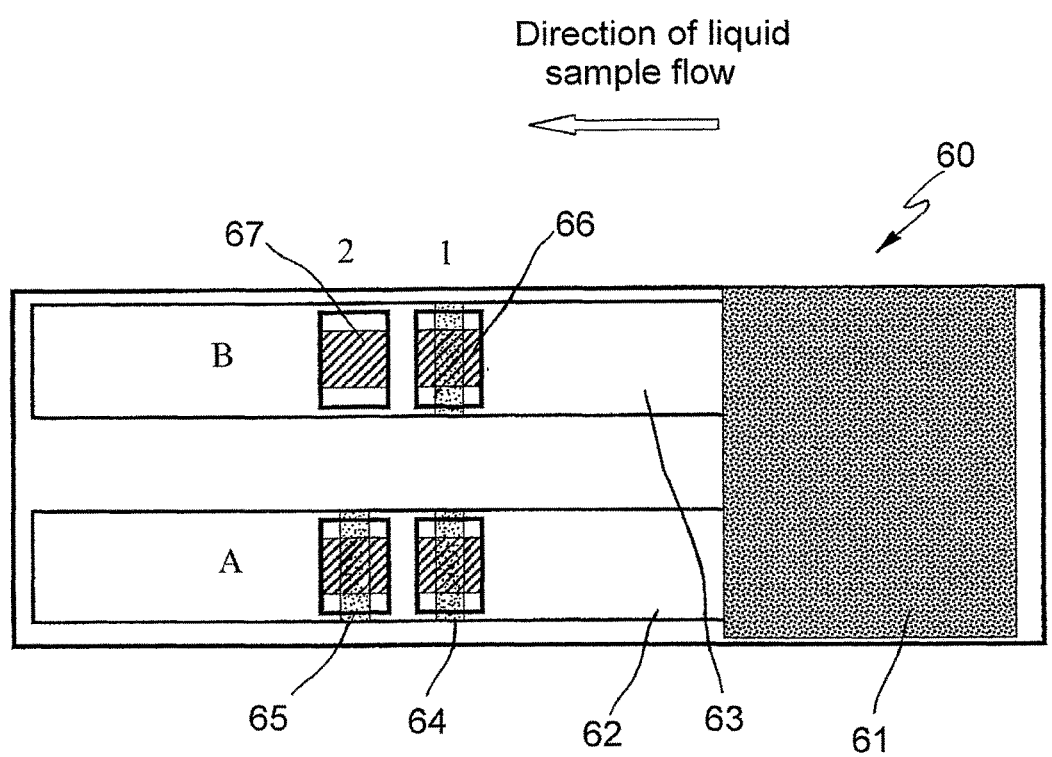
Figure 4A:
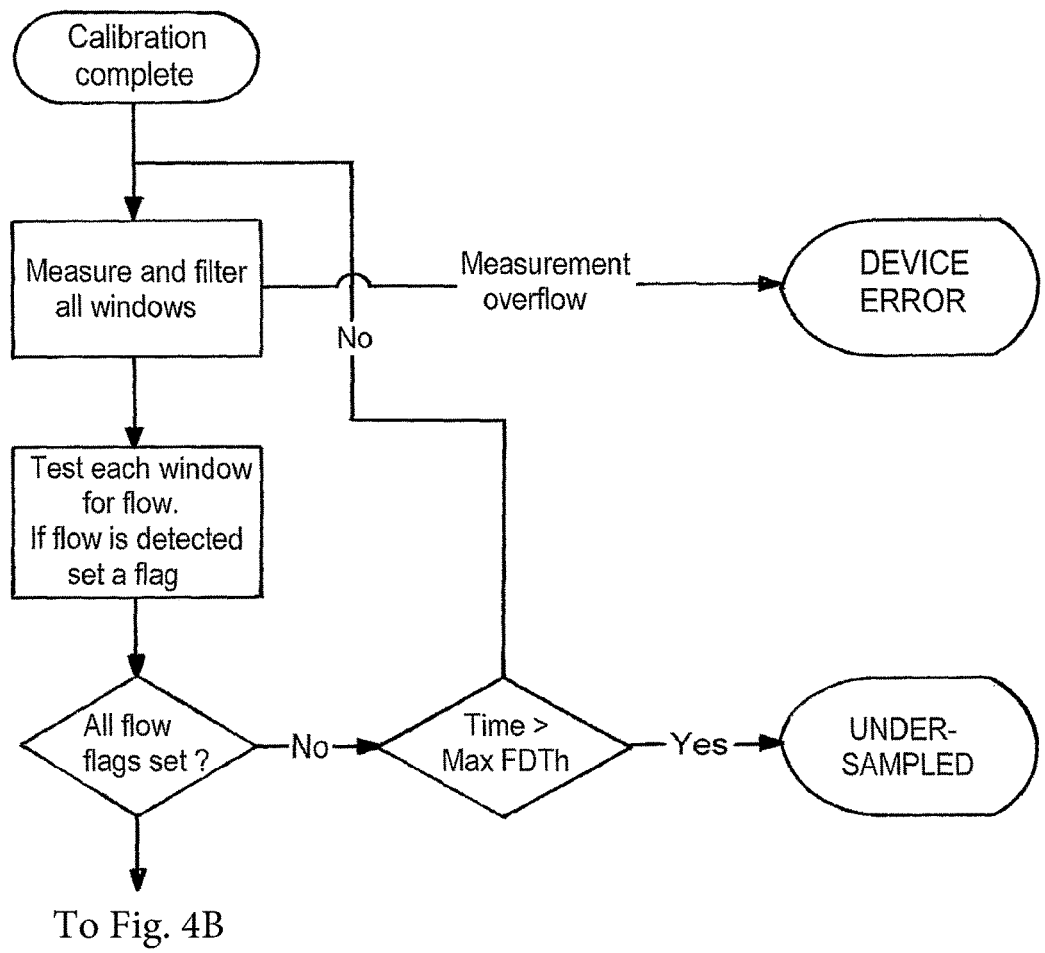
Figure 4B:
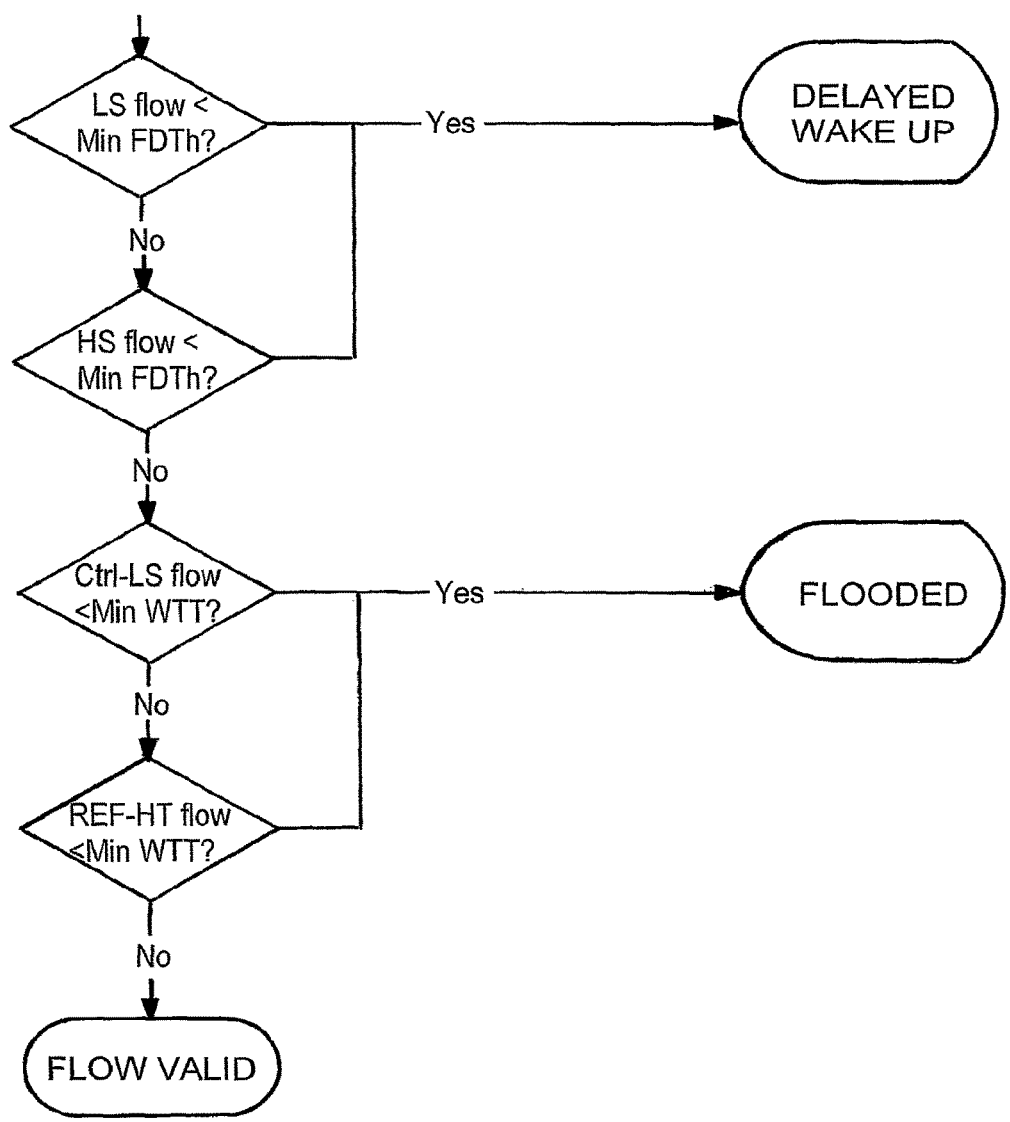

FIG. 3 shows an exemplary assay device according to an embodiment of the invention FIGS. 4A-B show an exemplary algorithm for determination of flow rate for an assay device comprising a high sensitive (HS) assay and a low sensitive (LS) assay.

Figure 5A:
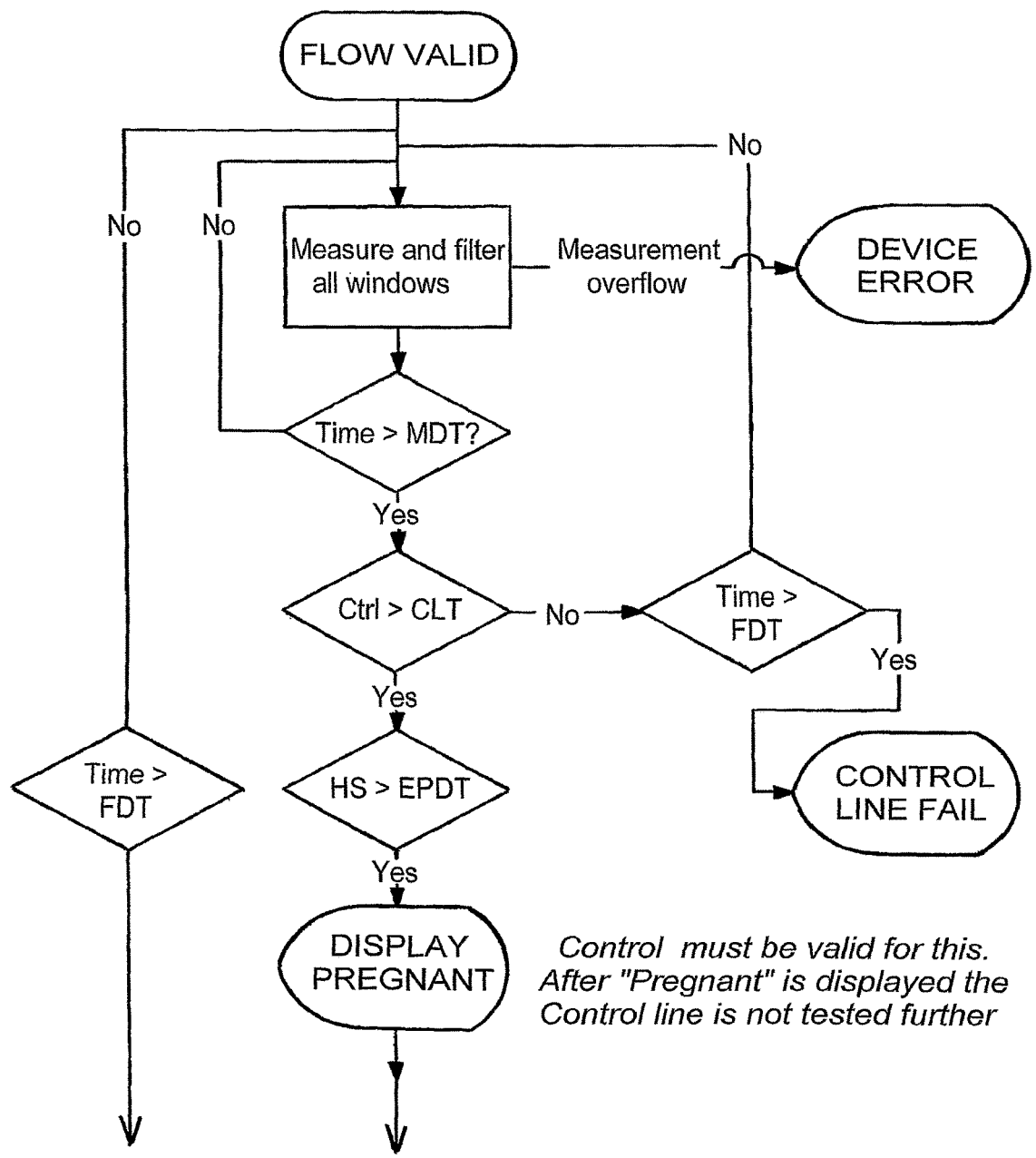
Figure 5B:
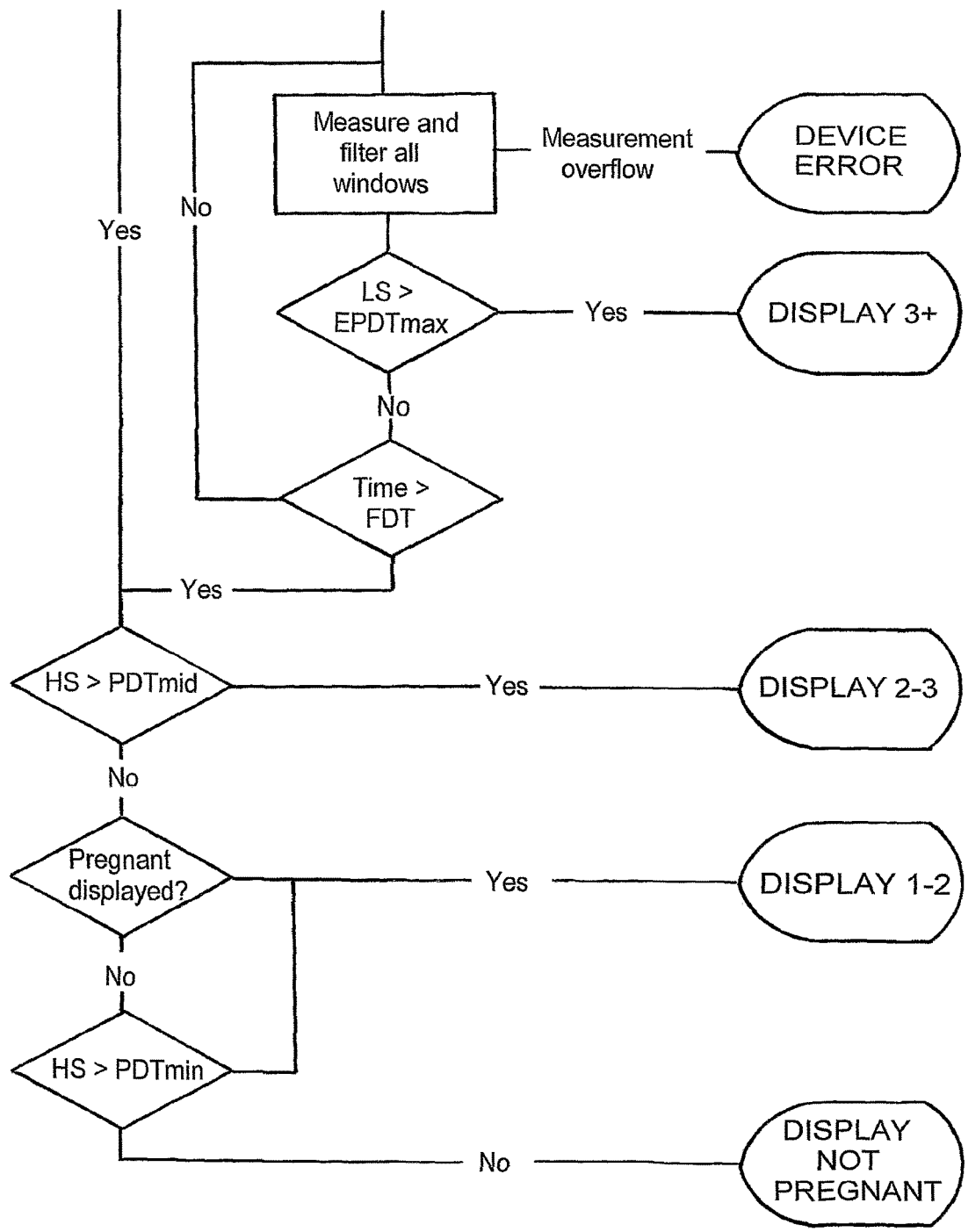

FIGS. 5A-B show an exemplary algorithm for the determination of a time since conception for an assay device comprising a high sensitive (HS) assay and a low sensitive (LS) assay.

Figure 6A:
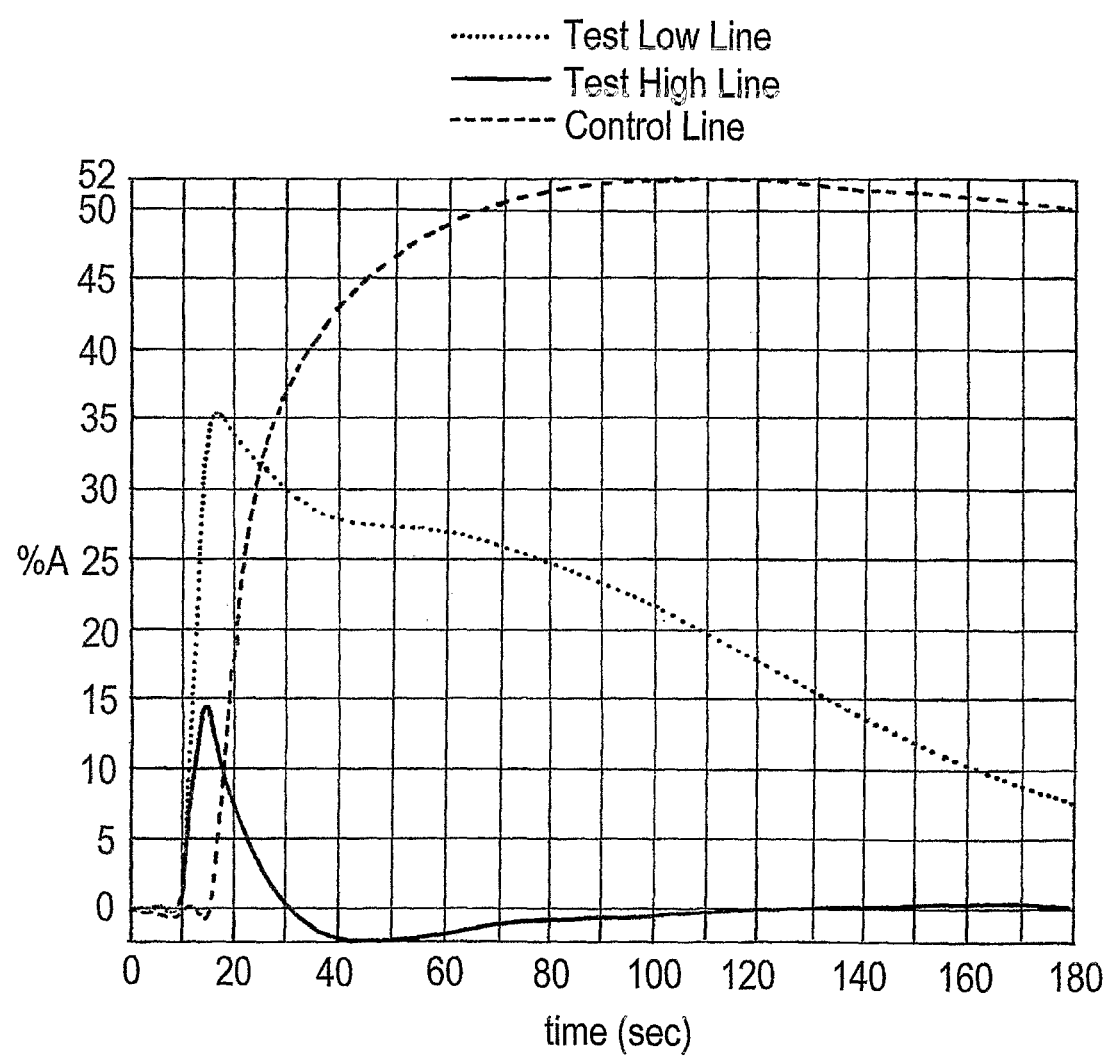
Figure 6:
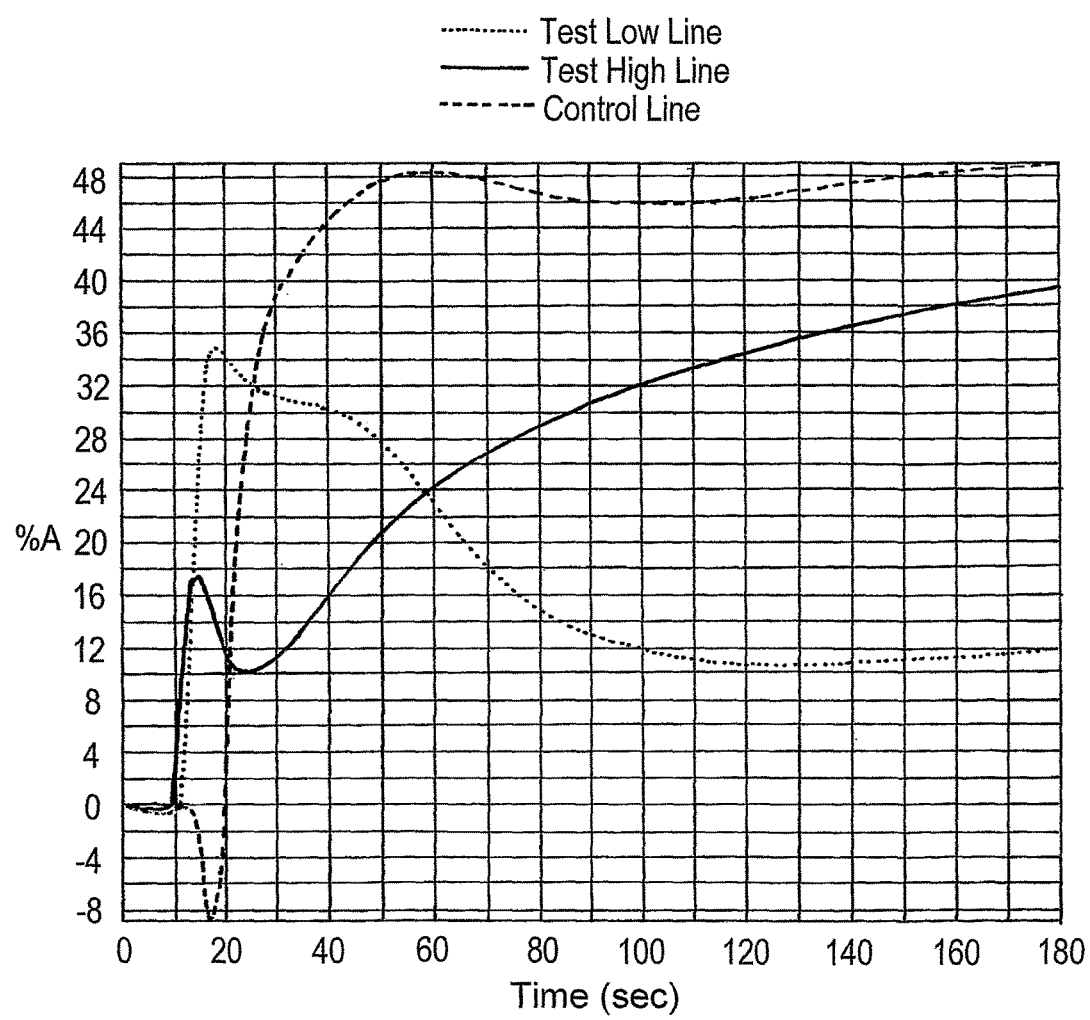
Figure 6C:
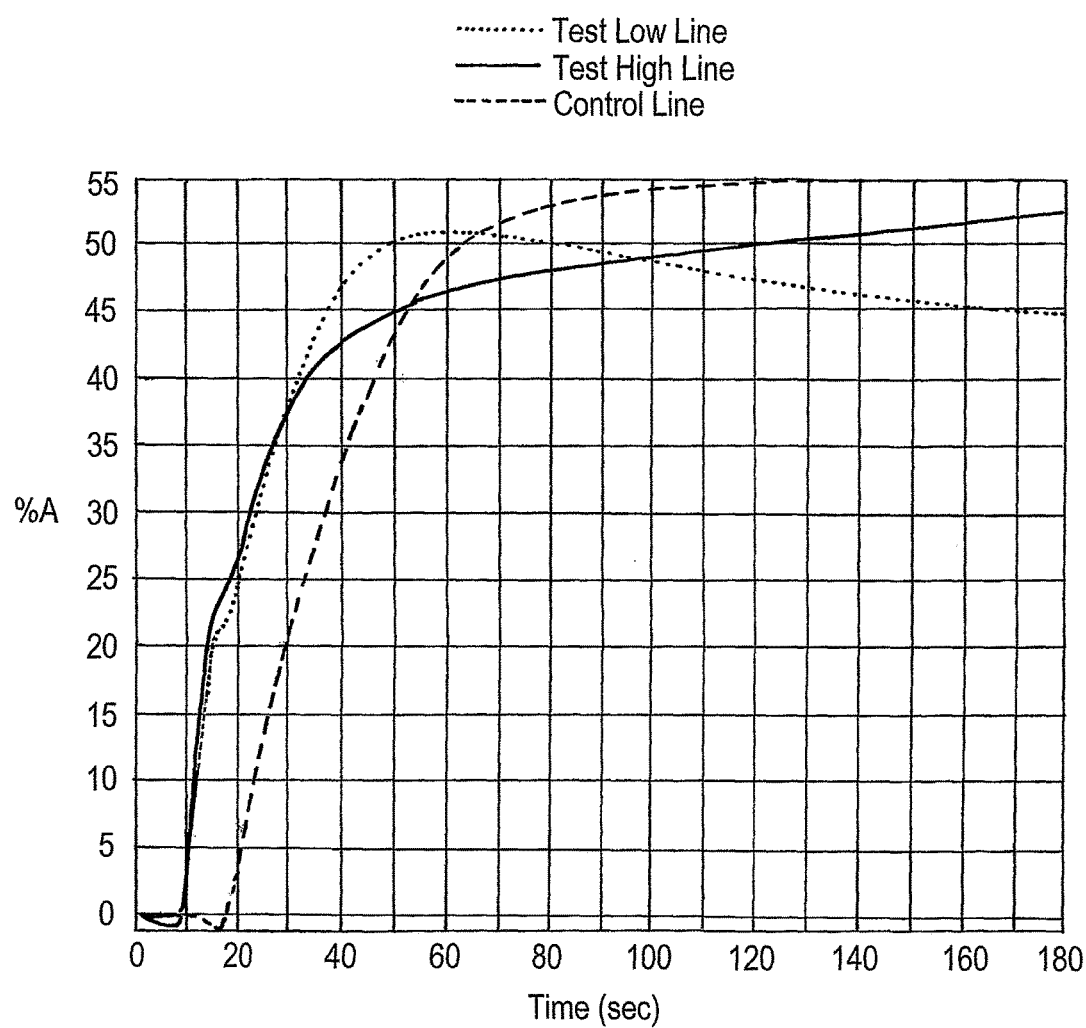
Figure 7:
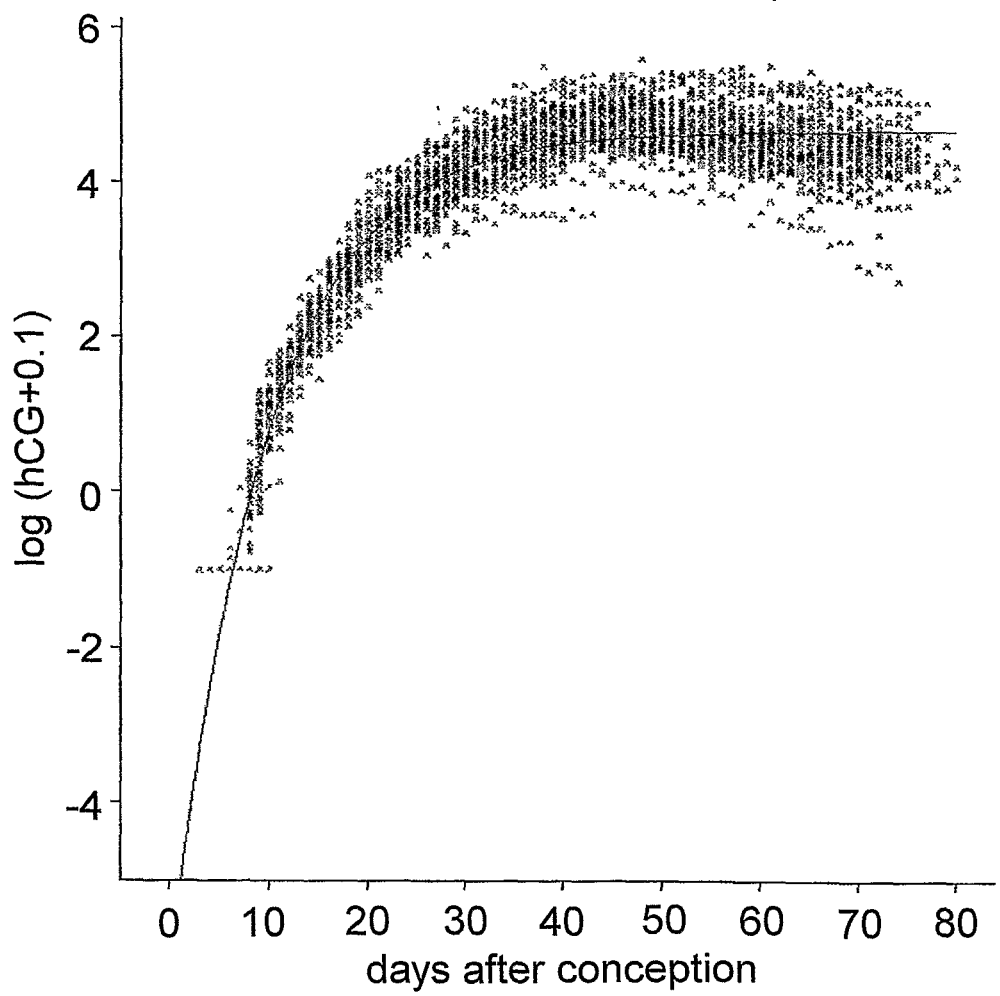

FIGS. 6(a)-(c) show typical % A vs. assay time profiles that are obtained for an assay device and method for the detection of hCG FIG. 7 shows the graph plotted for time since conception vs. log(hCG+0.1) obtained for a cohort of women and a fitted exponential curve according to Example 2.

Figure 8A:
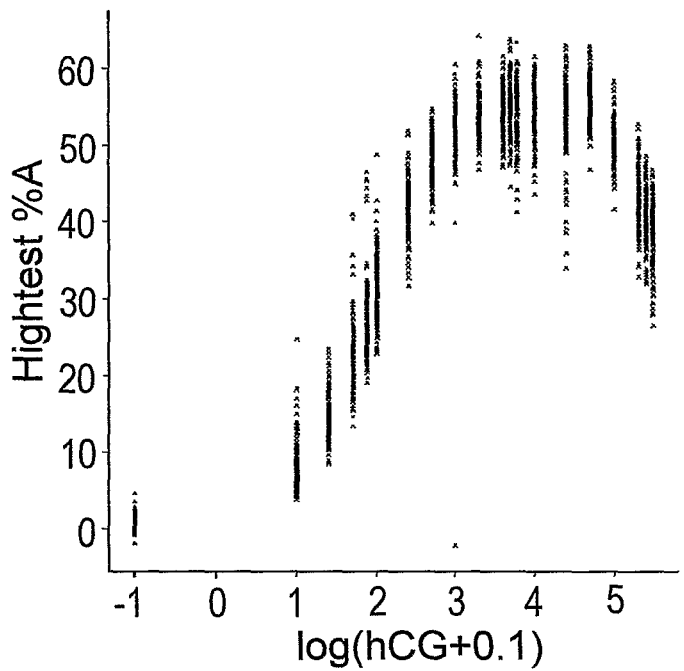
Figure 8B:
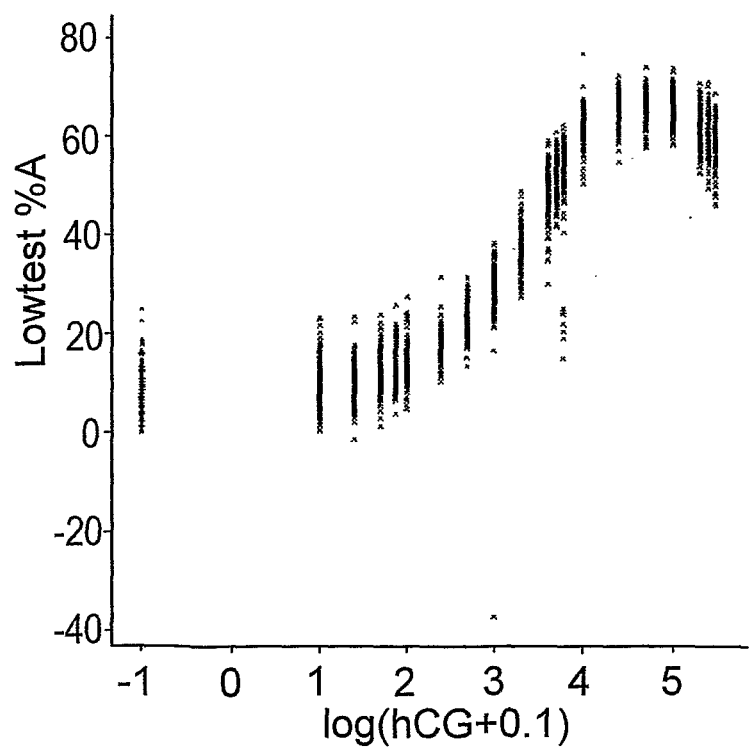

FIGS. 8(a) and (b) show the fitted and observed relationships for the high and low sensitivity assays prepared according to Example 1.

DETAILED DESCRIPTION OF THE FIGURES

Figure 2A:
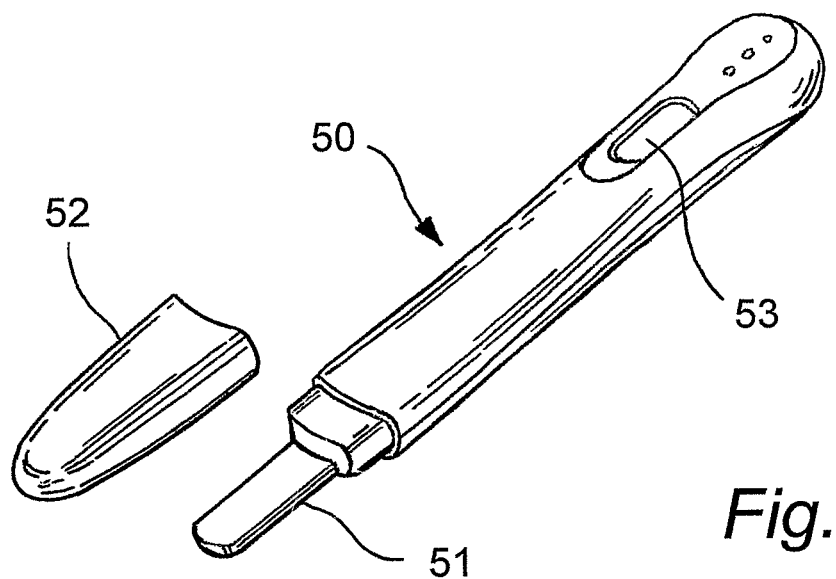

FIG. 2a shows an exemplary assay device of the invention. The device is elongate having a length of about 14 cm and a width of about 25 mm, comprising housing (50), a porous sample receiver (51) and an LCD display (53) for displaying the results of the assay. Also provided within the assay and not shown are the assay flow-paths, optical means, a power source and associated electronic components. The assay device may also have a removable cap (52) to fit over the porous sample receiver.

Figure 2B:
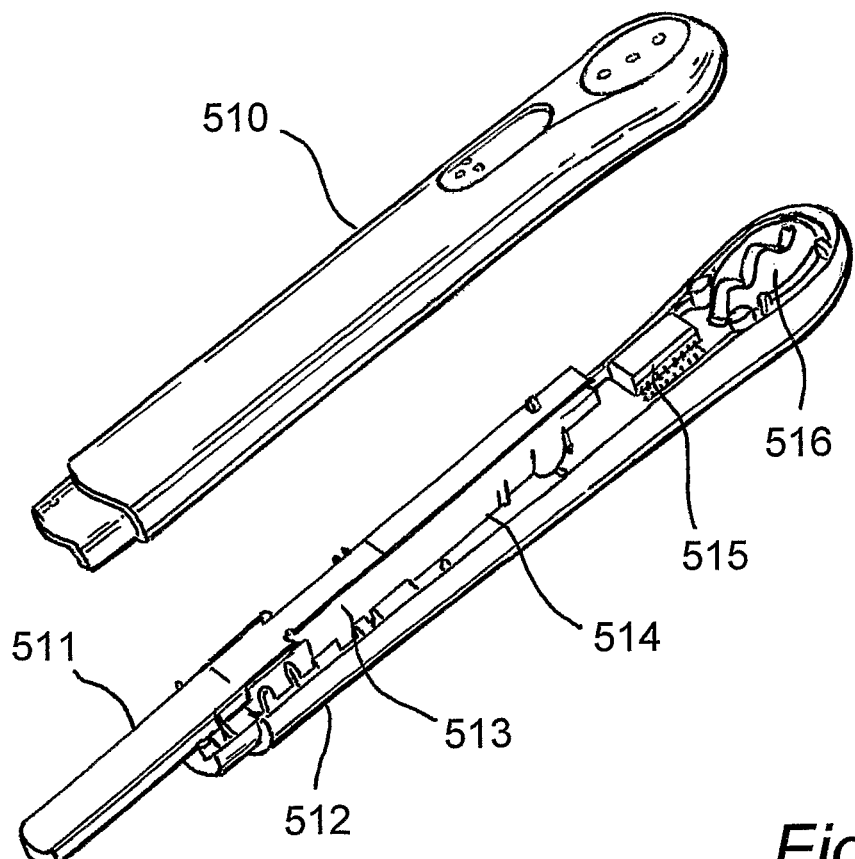

FIG. 2b shows an exemplary assay device according to the invention which has been opened to show some of the components. The device comprises upper and lower housings (510, 512), a desiccant tablet (513) to maintain low levels of humidity within the device, a battery (516) an optical baffle (514) and computer chip (515).

FIG. 3 shows the layout of the individual assay porous carriers of an assay device according to an exemplary embodiment having a shared control and reference zone. Assay device (60) has a common sample application region (61) which fluidically connects first and second assays (62) and (63). Zones (64) and (65) correspond respectively to a detection and control zone for the assay. Zones (66) and (67) correspond respectively to a detection and reference zone.

FIG. 4 shows an exemplary algorithm for determination of flow rate for an assay device comprising a high sensitivity (HS) assay and a low sensitivity (LS) assay.

Once the calibration is complete, all of the windows are measured and filtered.

The minimum flow detection time (Min FDT) may be defined as the minimum time that flow will reach one or more measurement zones. If flow is detected at times less than the minimum flow detection time, it is assumed that the device has "woken up" late and that any calibration values are likely to have been affected by flow already being present in the window during calibration. These devices may be classed as "late wake-up errors".

The maximum flow detection time (Max FDT) may be defined as a time by which liquid sample has to reach all of the measurement zones after having been applied to the device or after the device has been activated following application of liquid sample. If flow has not been detected in the all of the measurement zones before this maximum time from wake-up the device is assumed to be under sampled, namely not enough liquid sample has been applied to the assay device. These devices may be classed as being under sampled.

The minimum window transit time (Min WTT) may be defined as the minimum time by which fluid passes between one zone and downstream zone. Flow between the windows corresponding to these zones must occur by a minimum time difference. Flow times less than this time may be rejected as it is likely that the device has been flooded or over sampled.

The following is an example of the flow-rate parameters that may be employed:

| Parameter | Value |
|---|---|
| Minimum Flow Detection Time (Min FDT) | 3 seconds |
| Maximum Flow Detection Time (Max FDT) | 64 seconds |
| Minimum Window Transit Time (Min WTT) | 2 seconds |

FIG. 5 shows an exemplary algorithm for the determination of a time since conception for an assay device for the determination of hCG over an extended analyte range comprising a high sensitivity (HS) assay and a low sensitivity (LS) assay, each comprising a test zone.

Timing for the assay is from the point of detection of flow through the high sensitivity test line window. The algorithm provides for an early indication of "pregnant", earlier than the full assay test time. Indications of the time since conception or "not pregnant" are given at the full assay test time (full assay development time).

Once the flow has been determined to be valid by the flow algorithm parameter, after the minimum development time, if $HS_t$ (% A) exceeds the Early Pregnant Decision Threshold and $Ctrl_t$ (% A) is above the Control Line Threshold then a result of PREGNANT is displayed.

After the Minimum Development Time and PREGNANT is displayed, subsequently if $LS_t$ (% A) exceeds the Early Pregnant Max Decision Threshold then the conception guide indication for the maximum time (+3 weeks) is displayed. At Full Assay Development Time If by this time PREGNANT is already displayed then the control line is not tested. Otherwise if the control line is below the Control Line Threshold then "Device Error" is indicated and the test is complete.

If $HS_t$ (% A) exceeds the Pregnant Mid Decision Threshold then the conception guide indication for the mid time is displayed (2-3 weeks) and the test is complete.

If by this time PREGNANT is already displayed then the conception guide indication for the minimum time (1-2 weeks) is displayed and the test is complete. If $HS_t$ (% A) exceeds the Pregnant Minimum Decision Threshold (PDTmin) then PREGNANT and the conception guide indication for the minimum time is displayed and the test is complete.

Otherwise NOT PREGNANT is displayed and the test is complete.

An example of the particular decision algorithm parameters for an assay device for the detection of hCG that may be employed is as follows:

| Parameter | Value |
|---|---|
| Control Line Threshold (CLT) | 30% A |
| Minimum Development Time (MDT) | 60 seconds |
| Early Pregnant Decision Threshold (EPDT) | 14% A |
| Early Pregnant Max Decision Threshold (EPDTmax) | 45% A |
| Full Assay Development Time (FDT) | 150 seconds |
| Pregnant Mid Decision Threshold (PDTmid) | 25% A |
| Pregnant Min Decision Threshold (PDTmin) | 9% A |

In particular the decision algorithm parameters may be employed in the assay device according to example 1 for the detection of hCG. In particular the decision algorithm parameters may be employed in the assay device comprising a shared reference and control zone as illustrated in FIG. 3.

FIGS. 6 (a)-(c) show a typical signal profile of % A vs. time (s) obtained when testing assay devices according to Example 2 having a shared control and reference line according to FIG. 3 for varying levels of hCG in urine. FIGS. 6 (a)-(c) refer to assay devices tested with buffer solution containing respectively 0, 100 and 2000 mIU hCG.

The invention may be further characterised with reference to the following examples:

EXAMPLE 1

Preparation of an Assay Device Comprising a Low Sensitivity Assay and a High Sensitivity Assay for the Determination of hCG Over an Extended Analyte Range.

The high sensitivity assay was prepared for the determination of hCG analyte comprising a mobilisable labelled binding reagent for hCG on a glass fibre porous carrier provided upstream from a detection zone and a control zone provided on a nitrocellulose porous carrier The detection zone comprised immobilised binding reagent for hCG.

The detection zone was prepared by dispensing a line of anti-β-hCG antibody (in-house clone 3468) at a concentration of 3 mg/ml in PBSA buffer, at a rate of 1 μl/cm on onto bands of nitrocellulose of dimensions 350 mm length×40 mm width (Whatman) having a pore-size of 8 microns and a thickness between 90-100 microns which had been laminated to a 175 micron backing layer. The anti-β-hCG antibody was applied using the Biodot xyz3050 dispensing platform as a line ~1.2 mm in width and ~300 mm in length at a position of 10 mm along the length of the nitrocellulose.

The control zone was prepared plotting goat-anti-rabbit antibody (Lampire), 2 mg/ml in PBSA buffer at 1 μl/cm onto nitrocellulose at the 13 mm position, 3 mm downstream of the detection zone, using a Biodot XYZ3050 dispensing platform.

The bands of NC were dried using Hedinair drying oven serial #17494 set at 55° C. and speed 5 (single pass). The NC was then blocked using a blocking buffer comprising a mixture of 5% ethanol (BDH Analar 104766P) plus 150 mM Sodium Chloride (BDH Analar 10241AP) plus 50 mM trizma base from (Sigma T1503) plus Tween 20 (Sigma P1379) and 1% (w/v) polyvinyl alcohol (PVA, Sigma 360627). The blocking buffer was applied at a rate of 1.75 μl/mm to the proximal end of the band. Once the blocking solution had soaked into the membrane a solution of 2% (w/v) sucrose (Sigma S8501 in deionised water) was applied using the same apparatus at a rate of 1.6 μl/mm and allowed to soak into the nitrocellulose membrane for ~5 minutes). The bands of NC were then dried using a Hedinair drying oven serial #17494 set at 75° C. and speed 5 (single pass).

Preparation of the Labelled Binding Reagent for hCG.

Labelled binding reagent was prepared according to the following protocol:

Coating Latex Particles with Anti-α hCG

1. Dilute blue latex particles from Duke Scientific (400 nm in diameter, DB1040CB at 10% solids (w/v)) to 2% solids (w/v) with 100 mM di-sodium tetra borate buffer pH 8.5 (BDH AnalaR 102676G) (DTB).
2. Wash the diluted latex by centrifuging a volume of (2 mls) of diluted latex in two Eppendorf centrifuge tubes at 17000 rpm (25,848 rcf) for 10 minutes on an Heraeus Biofuge 17RS centrifuge. Remove and discard the supernatant and re-suspend the pellets in 100 mM DTB to give 4% solids (w/v) in a total volume of 1 ml.
3. Prepare a mixture of ethanol and sodium acetate (95% Ethanol BDH AnalaR 104766P with 5% w/v Sodium Acetate Sigma S-2889).
4. Add 100 μls ethanol-sodium acetate solution to the washed latex in step 2 (this is 10% of the volume of latex).
5. Dilute the stock antibody (in-house clone 3299) to give ~1200 μg/ml antibody in DTB.
6. Heat a volume of 1 ml of the diluted antibody from step 5 in a water bath set at 41.5° C. for ~2 minutes. Also heat the washed latex plus ethanol-sodium acetate from step 4 in the same water bath for 2 minutes.
7. Add the diluted antibody to the latex plus ethanol-acetate, mix well and incubate for 1 hour in the water bath set at 41.5° C. whilst mixing using a magnetic stirrer and a magnetic flea placed in the mixture.
8. Prepare 40 mg/ml Bovine Serum Albumin (BSA) Solution (Intergen W22903 in de-ionised water). Block the latex by adding an equal volume of 40 mg/ml BSA to the mixture of latex/antibody/ethanol-acetate and incubate in the water bath at 41.5° C. for 30 minutes with continued stirring.
9. Centrifuge the mixture at 17000 rpm for 10 minutes as in step 2, (split the volume into 1 ml lots between Eppendorf tubes). Remove and discard the supernatant and re-suspend the pellet in 100 mM DTB. Repeat the centrifugation as in step 2, remove and discard the supernatant and re-suspend in pellet in Air Brushing Buffer (20% (w/v) Sucrose Sigma S8501, 10% BSA (w/v) in 100 mM Trizma Base Sigma T1503 pH to 9). Add Air Brushing Buffer to give 4% solids (w/v) latex.

The conjugated latex was and sprayed in a mixture of BSA and sucrose onto a glass-fibre porous carrier (F529-09, Whatman) at a rate of 50 g/hr and 110 mm/s and dried using a Hedinar Conveyor Oven Serial number 17494 set at 65° C. and speed 5 (single pass).

Labelled binding reagent for the control zone was also deposited onto the same region of the porous carrier as the labelled binding reagent for the analyte as follows: Rabbit IgG (Dako) was conjugated to 400 nm blue latex polystyrene latex (Duke Scientific) in BSA/sucrose to give a final % blue latex of 0.7% solids and sprayed at 65 g/hr onto glass fibre.

The glass fibre material with sprayed labelled binding reagent was attached to the nitrocellulose membrane using a clear adhesive coated laminate film (Ferrisgate, 38 mm wide) arranged such that the labelled reagent was uppermost and the glass fibre overlapped the surface of the nitrocellulose by ~2 mm along the length (350 mm) of the band of nitrocellulose membrane. The glass fibre was attached to the end of the nitrocellulose such that it was upstream of the detection zone.

The zone chosen as the reference zone was at a distance of 13 mm along the nitrocellulose, namely downstream of the detection zone.

The laminated sheet was subsequently cut into test-strips of 6 mm width.

The low sensitivity assay for the determination of hCG was prepared comprising a mobilisable labelled binding reagent for hCG and a mobilisable second binding reagent for hCG on a glass fibre porous carrier provided upstream from a detection zone and a control zone provided on a nitrocellulose porous carrier. The detection zone comprised immobilised binding reagent for hCG.

The detection zone was prepared according to that of the high sensitivity assay.

The control zone was prepared plotting goat-anti-rabbit antibody (Lampire), 2 mg/ml in PBSA buffer at 1 μl/cm onto nitrocellulose at the 13 mm position, 3 mm downstream of the detection zone, using a Biodot XYZ3050 dispensing platform.

Preparation of the Mobilisable Labelled and Second Binding Reagents

Mouse-anti-human α-hCG mAb (clone 3299) conjugated to 400 nm blue polystyrene latex (Duke Scientific) was mixed with scavenger antibody mAb mouse anti-human β-hCG (in-house clone 3468) at 3 mg/ml to give a final % blue latex of 3%, a final 3468 concentration of 0.075 mg/ml and 0.06 mg/ml concentration of the free anti-β hCG antibody. The resulting mixture was airbrushed onto Whatman glass fibre (F529 25 mm wide reels) using the BIODOT XYZS (serial number 1673) at 90 g/hr sprayed at 2.02 μg/cm onto F529-09 glass fibre.

Labelled binding reagent for the control zone was also deposited onto the same region of the porous carrier as the labelled binding reagent for the analyte as follows: Rabbit IgG (Dako) was conjugated to 400 nm blue latex polystyrene latex (Duke Scientific) in BSA/sucrose to give a final % blue latex of 0.7% solids and sprayed at 65 g/hr onto glass fibre.

The glass fibre was dried using a Hedinar Conveyor Oven Serial number 17494 set at 65° C. and speed 5 (single pass). A second pass of latex was deposited onto the glass fibre by repeating the above however at an offset of ~0.8 mm from the original position of spray (further downstream of the glass fibre). The glass fibre was subsequently dried using a Hedinar Conveyor Oven Serial number 17494 set at 65° C. and speed 5 (single pass).

The glass fibre material with sprayed labelled binding reagent was attached to the nitrocellulose membrane using a clear adhesive coated laminate film (Ferrisgate, 38 mm wide) arranged such that the labelled reagent was uppermost and the glass fibre overlapped the surface of the nitrocellulose by ~2 mm along the length (350 mm) of the band of nitrocellulose membrane. The glass fibre was attached to the end of the nitrocellulose such that it was upstream of the detection zone.

The laminated sheet was subsequently cut into test-strips of 6 mm width.

A common porous sample receiver (505521, Filtrona Fibertech) of 45 mm length, 12 mm width and a thickness of approximately 2.5 mm was provided upstream from and overlapping the first and second assays by approximately 3 mm.

The high and low sensitivity assays were housed in an assay housing with the porous sample partially extending from the housing.

Signals were measured from the respective detection zones and control zone and were measured with respect to the signal measured from the shared reference zone.

As an alternative to providing shared control and reference zones, the high and low sensitivity assay may each comprise a reference and/or control zone.

EXAMPLE 2

The Determination of Threshold Values to be Stored in an Assay Device or Reader in Order to Determine a Date Since Conception.

A number of women aged between 18-45 were recruited into a study and selected on the basis that they were having regular menstrual cycles between 21-42 days over the last 6 months, were not breastfeeding, had no known history of infertility, not suffering from polycystic ovarian syndrome, not suffering from chronic renal or liver disease, and either not to have been using hormonal contraceptives during the past 3 months with at least three cycles since discontinuing. The women provided daily samples of urine over a minimum of six cycles and carried out daily measurements of their urinary LH levels using a Unipath FAM™ monitor to monitor and record the date of their LH surge as well as a diary to record the first day of their last menstrual period. Of the 61 women who became pregnant during the study, their, their urinary levels of hCG were measured on a daily basis up to 90 days post the date of their LH surge using an Perkin Elmer AutoDelphia laboratory analyser. Knowing the date of the LH surge for those pregnant individuals, a data set was generated of the measured level of hCG for each individual woman as a function of the date since conception, wherein the date of conception was defined as the date of the LH surge+1 day.

An exponential curve was used to model log(hCG+0.1) over time of pregnancy,
Wherein:

$$\log(hCG+0.1) = A + B*Rx$$

A (Max)
B (Diff between intercept and Max)
R (rate of increase)
x=time of pregnancy The raw data and fitted exponential curve is shown in FIG. 7.

31 urine samples from non-pregnant women were selected and spiked with hCG at 20 concentrations ranging from 10-250,000 mIU/ml hCG. Each spiked sample was applied to six assay devices chosen from three batches according to Example 1. Analyte signal values (% A) for the high and low sensitivity assays were measured as a function of hCG concentration at an FDT of 150 s.

A four parameter logistic curve was used to model % A for both the high sensitivity assay and the low sensitivity assay over the log(hCG+0.1) concentrations.
Where:

$$\% A = A + \frac{C}{(1 + e^{-B*(Log(hCG+0.1)-M)})}$$

And wherein
B=slope
M=log(hCG+0.1) level that results in a response half way between the minimum and maximum
C=difference between maximum and minimum
A=minimum The fitted and observed relationships for the high and low sensitivity assays are shown in FIGS. 8(a) and (b).

A simulation study was designed to optimise the PDTmin, PDTmid and EPDTmax thresholds in order to maximize the classification of pregnancies into three groups, <=2 wks since conception, 2-3 wks since conception and >3 wks since conception and to quantify the accuracy of the classification using these thresholds.

The thresholds were assessed against the results of real samples from five pregnant subjects in order to determine their accuracy.

The simulation was performed in three steps:
Step 1

Perform the simulation at a broad range of thresholds. The initial thresholds were chosen using prior knowledge of the device and the boundaries between groups as predicted from the exponential model from the first data set.
PDTmin (%)—5, 7.5, 10
PDTmid (%)—30, 32.5, 35
EPDTmax (%)—43, 45, 47

The choice of 3 values for each threshold provided 27 threshold combinations to be simulated.

Step 2

Pick the best combination of thresholds in Step 1 and look at narrower range of thresholds around the best combination.

Step 3

Choose the best combination of thresholds in Step 2 as the optimal set and do a more refined quantification.

The exponential model from the first data set and the two four parameter logistic models from the urine study (FDT=150 secs) in the second data set were used in the simulation process.

10,000 post-concept time points were generated from a uniform distribution for each of the following intervals:
7 to 10 (7 to 9 days)
10 to 15 (10 to 14 days)
15 to 22 (2-3 weeks)
22 to 43 (3+ weeks (up to 42 days));
wherein time is continuous and boundaries are points in time.

For each generated time point, log(hCG+0.1) was simulated. For each simulated log(hCG+0.1) value, a value for the lowtest and hightest % A values were calculated and for each pair of % A values the predicted conception guide outcome was calculated using a set of thresholds.

At step 3 a more refined simulation was performed with 10,000 post-concept time points generated from a uniform distribution for each day from day 7 to day 42. Each sampling interval went from midnight to midnight e.g. day 7 generated data were real numbers between 7 and 8.

Based upon the study, threshold values in % A were calculated for PDTmin, PDTmax and EPDTmax. These threshold values may be stored in the assay device or reader in order to calculate a time since conception.

The invention claimed is:

1. An electronic pregnancy test device for calculating a quantitative estimate of the length of time since conception in a female mammalian subject, the device comprising:
    a) a first assay flow-path, comprising a mobilizable labeled binding reagent for hCG, and a detection zone;
    b) a second assay flow-path, comprising a mobilizable labeled binding reagent for hCG and a second binding reagent for hCG, wherein the second binding reagent for hCG alters the sensitivity of an assay for hCG, and a detection zone, such that the first assay flow-path detection zone is for measuring hCG in a lower concentration range and the second assay flow-path detection zone is for measuring hCG in a higher concentration range;
    c) a processor;
    d) a first stored analyte threshold corresponding to a first time since conception, a second stored analyte threshold corresponding to a second time since conception, which is a longer period of time than that corresponding to the first stored analyte threshold, and a third stored analyte threshold which is a minimum pregnancy threshold, said analyte thresholds being stored in said electronic pregnancy test device and accessible to the processor;
    e) a shared reference zone, the shared reference zone being located within the first or second assay flow-path, the other of the first or second assay flow path having no reference zone located therein, wherein the value of a signal obtained at the shared reference zone compensates the value of a signal obtained at the detection zone of the other of the first or second assay flow-path;
    f) a measurement means for measuring a first analyte signal value from said first assay flow-path, and for measuring a second analyte signal value from said second assay flow-path, said first and second analyte signal values corresponding to the level of hCG in a liquid sample obtained from said subject, and comparing said first and/or second analyte signal values to the first, second, or third stored analyte thresholds, wherein a second analyte signal value greater than the second stored threshold indicates the subject is 3+ weeks pregnant; a second analyte signal value less than said second stored threshold but a first analyte signal value greater than the first stored threshold indicates the subject is 2-3 weeks pregnant; a first analyte signal value less than the first stored threshold but greater than the third stored threshold indicates the subject is 1-2 weeks pregnant; and a first analyte signal value less than the third stored threshold indicates that the subject is not pregnant; and
    g) a display means to display a result of the assay which is the quantitative estimate of the length of time since conception.

2. The test device according to claim 1, which further comprises one or more additional stored analyte thresholds corresponding to one or more times since conception.

3. The test device according to claim 1, wherein the first assay flow-path and the second assay flow-path each comprise a single detection zone.

4. The test device according to claim 1, further comprising a shared control zone located within the first or second assay flow-path, the other of the first or second assay flow-path having no control zone located therein, wherein measurement of a signal at the shared control zone provides a value or indication that the assay has been carried out correctly.

5. The test device according to claim 1, wherein the measurement means comprises a single photodetector to detect light from both detection zones, and four light sources to illuminate respectively the shared reference zone, a shared control zone and the two detection zones.

6. The test device according to claim 1, wherein the shared reference zone is provided downstream of the detection zone for the first or second assay flow-path.

7. The test device according to claim 1, wherein one or both assay flow-paths comprises a lateral flow porous carrier.

8. The test device according to claim 7, wherein the lateral flow porous carrier comprises nitrocellulose.

9. The device of claim 1, wherein the second analyte signal value is diminished compared to the first analyte signal value due to the presence of the second binding reagent for hCG, which diminishes the amount of hCG available to be bound at the detection zone relative to the first assay flow-path.

10. The device of claim 1, wherein the first assay flow-path or the second assay flow-path comprises a control zone downstream of their respective detection zones.

11. The device of claim 10, wherein the control zone is a shared control zone.

12. The device of claim 10, wherein a signal value determined at the control zone is used to validate the result of the first and second assay flow-paths respectively.

13. The device of claim 1, wherein the reference zone is downstream of the detection zone within the first or second assay flow-path.

14. An electronic pregnancy test device for calculating a quantitative estimate of the length of time since conception in a female mammalian subject, the device comprising:

a) a first assay flow-path, comprising a mobilizable labeled binding reagent for hCG, and a detection zone;
b) a second assay flow-path, comprising a mobilizable labeled binding reagent for hCG and a second binding reagent for hCG, wherein the second binding reagent for hCG alters the sensitivity of an assay for hCG, and a detection zone, such that the first assay flow-path detection zone is for measuring hCG in a lower concentration range and the second assay flow-path detection zone is for measuring hCG in a higher concentration range;
c) a processor;
d) a first stored analyte threshold corresponding to a first time since conception, a second stored analyte threshold corresponding to a second time since conception, which is a longer period of time than the first stored analyte threshold, and a third stored analyte threshold which is a minimum pregnancy threshold, said analyte thresholds being stored in said electronic pregnancy test device and accessible to the processor;
e) a shared reference zone, the shared reference zone being located within a subsidiary flow-path to the first and second assay flow-paths, the first and second assay flow-paths having no reference zone located therein, wherein the value of a signal obtained at the shared reference zone compensates the value of signals obtained at the detection zones of the first and second assay flow-paths;
f) a measurement means for measuring a first analyte signal value from said first assay flow-path, and for measuring a second analyte signal value from said second assay flow-path, said first and second analyte signal values corresponding to the level of hCG in a liquid sample obtained from said subject, and comparing said first and/or second analyte signal values to the first, second, or third stored analyte thresholds, wherein a second analyte signal value greater than the second stored threshold indicates the subject is 3+ weeks pregnant; a second analyte signal value less than said second stored threshold but a first analyte signal value greater than the first stored threshold indicates the subject is 2-3 weeks pregnant; a first analyte signal value less than the first stored threshold but greater than the third stored threshold indicates the subject is 1-2 weeks pregnant; and a first analyte signal value less than the third stored threshold indicates that the subject is not pregnant; and g) a display means to display a result of the assay which is the quantitative estimate of the length of time since conception.

15. The test device according to claim 14, which further comprises one or more additional stored analyte thresholds corresponding to one or more times since conception.

16. The test device according to claim 14, wherein the first assay flow-path and the second assay flow-path each comprise a single detection zone.

17. The test device according to claim 14, further comprising a shared control zone located within the first or second assay flow-path, the other of the first or second assay flow-path having no control zone located therein, wherein measurement of a signal at the shared control zone provides a value or indication that the assay has been carried out correctly.

18. The test device according to claim 14, wherein the measurement means comprises a single photodetector to detect light from both detection zones, and four light sources to illuminate respectively the shared reference zone, a shared control zone and the two detection zones.

19. The test device according to claim 14, wherein the shared reference zone is provided downstream of the detection zone for the first or second assay flow-path.

20. The test device according to claim 14, wherein one or both assay flow-paths comprises a lateral flow porous carrier.

21. The test device according to claim 20, wherein the lateral flow porous carrier comprises nitrocellulose.

22. The test device according to claim 14, wherein the second analyte signal value is diminished compared to the first analyte signal value due to the presence of the second binding reagent for hCG, which diminishes the amount of hCG available to be bound at the detection zone relative to the first assay flow-path.

23. The test device according to claim 14, wherein the first assay flow-path or the second assay flow-path comprises a control zone downstream of their respective detection zones.

24. The test device according to claim 23, wherein the control zone is a shared control zone.

25. The test device according to claim 23, wherein a signal value determined at the control zone is used to validate the result of the first and second assay flow-paths respectively.

26. The test device according to claim 14, wherein the reference zone within the first or second assay flow-path is downstream of the detection zone.

* * * * *